(12) United States Patent
Lazzari et al.

(10) Patent No.: US 7,294,714 B2
(45) Date of Patent: Nov. 13, 2007

(54) HIGHLY COMPATIBLE HYDROXYPHENYLTRIAZINE UV-ABSORBERS

(75) Inventors: Dario Lazzari, Bologna (IT); David George Leppard, Marly (CH); Massimiliano Sala, Modena (IT); Manuele Vitali, Bologna (IT); Graziano Zagnoni, Vergato (IT); Gianluca Ferri, Anzola Emilia (IT)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 30 days.

(21) Appl. No.: 11/525,267

(22) Filed: Sep. 22, 2006

(65) Prior Publication Data

US 2007/0161726 A1    Jul. 12, 2007

Related U.S. Application Data

(63) Continuation of application No. 10/482,680, filed as application No. PCT/EP02/07013 on Jun. 25, 2002, now abandoned.

(30) Foreign Application Priority Data

Jul. 2, 2001 (EP) ................................. 01810644
Nov. 30, 2001 (EP) ................................. 01811163

(51) Int. Cl.
*C07D 251/24* (2006.01)
*C08K 5/3467* (2006.01)

(52) U.S. Cl. ................. 544/216; 252/301.23; 524/100; 424/59

(58) Field of Classification Search ................. 544/216; 524/100; 252/301.23; 424/59
See application file for complete search history.

(56) References Cited

U.S. PATENT DOCUMENTS

| | | | |
|---|---|---|---|
| 3,244,708 A | 4/1966 | Duennenberger et al. ... | 260/248 |
| 4,826,978 A | 5/1989 | Migdal et al. ............... | 544/216 |
| 5,106,891 A | 4/1992 | Valet ........................... | 524/91 |
| 5,322,868 A | 6/1994 | Valet et al. .................. | 524/89 |
| 5,686,233 A | 11/1997 | Valet et al. ................. | 430/512 |
| 5,688,995 A * | 11/1997 | Luther et al. ................. | 562/30 |
| 5,736,597 A | 4/1998 | Birbaum et al. ............ | 524/100 |
| 5,824,465 A | 10/1998 | Marien et al. .............. | 430/631 |
| 5,959,008 A | 9/1999 | Birbaum et al. ............ | 524/100 |
| 5,962,452 A | 10/1999 | Haase et al. ................. | 514/241 |
| 6,166,148 A | 12/2000 | Ohrbom et al. .......... | 525/326.7 |
| 6,191,199 B1 * | 2/2001 | Renz et al. ................. | 524/100 |
| 6,242,597 B1 | 6/2001 | Gupta et al. ................ | 544/216 |
| 6,284,821 B1 | 9/2001 | Hüglin et al. ............... | 524/100 |

FOREIGN PATENT DOCUMENTS

| | | |
|---|---|---|
| EP | 0434608 | 6/1991 |
| EP | 0878469 | 11/1998 |
| EP | 0941989 A2 * | 9/1999 |
| GB | 2317174 | 3/1998 |
| GB | 2367824 | 4/2002 |
| WO | 94/18278 | 8/1994 |
| WO | WO-96/28431 A1 * | 9/1996 |
| WO | 99/26935 | 6/1999 |

* cited by examiner

*Primary Examiner*—Venkataraman Balasubramanian
(74) *Attorney, Agent, or Firm*—Tyler A. Stevenson

(57) ABSTRACT

The present invention relates to highly compatible hydroxyphenyltriazine UV-absorbers and to their use in protecting plants in green houses and the protection of foodstuffs, beverages, pharmaceuticals, cosmetics, personal care products, shampoos and the like from the deleterious effects of ultraviolet radiation. It has been found that certain highly compatible tris-aryl-s-triazines are especially effective towards this end when incorporated in the containers or films in which such materials are stored.

14 Claims, No Drawings

HIGHLY COMPATIBLE HYDROXYPHENYLTRIAZINE UV-ABSORBERS

This is a continuation of application Ser. No. 10/482,680, filed Jun. 30, 2004 abandoned, which is a 371 of international application PCT/EP02/07013, filed Jun. 25, 2002, the contents of which are hereby incorporated by reference.

The present invention relates to highly compatible hydroxyphenyltriazine UV-absorbers and to organic polymer material containing them, especially for use in protecting plants in greenhouses and for protecting packed foodstuffs, beverages, pharmaceuticals, cosmetics, personal care products, shampoos and the like from the deleterious effects of ultraviolet radiation. It has been found that certain highly compatible tris-aryl-s-triazines are especially effective towards this end when incorporated in the containers or films in which such materials are stored.

It is well known in the art that some types of crops are degraded by the UV-components of solar radiation which must be filtered off to obtain high quality and productivity of the crops. Additionally, some microorganisms, e.g. *Botrytis Cinerea*, as well as some harmful insects, e.g. white flies, aphides, thrips or leafminers, can proliferate under specific UV-irradiation. These pest can be significantly reduced when UV light does not or to less extent reach the plants. [R. Reuveni et al., *Development of photoselective PE films for control of foliar pathogens in greenhouse-grown crops*, Plasticulture No. 102, p. 7 (1994); Y. Antignus et al., *The use of UV absorbing plastic sheets to protect crops against insects and spread of virus diseases*, CIPA Congress March 1997, pp. 23-33]. On the other hand, bee activity, requiring a certain band of UV radiation, needs to be retained in greenhouses in order to ensure fructification on flowering plants, e.g. tomato, cucumber, pumpkin etc.

Also many packaged products such as certain fruit juices, soft drinks, beer, wines, food products, dairy products, cosmetics, shampoos, vitamins and pharmaceuticals are deleteriously affected, i.e. degraded, by the effects of ultraviolet (UV) light when packaged in plastic containers which allow the transmission of such light.

The use of UV absorbers towards protecting bottle and film contents is well known. However there is a trend towards the use of clear or lightly colored containers. More aesthetically pleasing containers may be formed from clear plastics which also allow one to view the contents. Unfortunately, clear and lightly colored containers and films allow the transmission of significant portions of ultraviolet light, i.e. light in the range of about 280 to about 400 nm. Further, there is a trend towards more light-weight and hence thinner walled containers. Thin-walled containers, by virtue of a shorter path length, will allow more UV light to pass. Due to these trends in packaging there is a need for more efficient UV absorbers for use in this area.

Many cooking oils and salad oils are now offered in clear PET [poly(ethylene terephthalate)] packaging. Practically all vegetable or seed-based oils such as soybean, olive, safflower, cottonseed and corn oils contain varying levels of unsaturated olefinic acids or esters (e.g. linoleates) which are susceptible to light-induced degradation. Most plant based oils also contain natural chlorophyll or other pigment photosensitizers. Pascall, et al., *J. Food Sci.*, 60 (5), 1116 (1995), discuss the UV protection of soybean oil with the use of Tinuvine® 326 incorporated into coextruded, multi-layered, polypropylene-based containers. Tinuvine® 326 is a benzotriazole UV absorber, 5-chloro-2-(2-hydroxy-3-tert-butyl-5-methyl-phenyl)-2H-benzotriazole, available from Ciba Specialty Chemicals Corp.

Present hydroxyphenyl triazine UV absorbers show excellent compatibility and persistence in a variety of plastic materials and protect these materials from the harmful effects of UV radiation. The same time, these UV absorbers provide efficient and selective UV shielding in greenhouse films, window sheets and packaging materials. Due to their extremely long alkyl chains they are highly compatible with many polymers, allowing thus to incorporate higher amounts of UVA. They are thermally stable and do not exude from the polymer, which is important when in contact with food or beverages.

The present invention relates to a hydroxyphenyltriazine of formula (I) or (Ib)

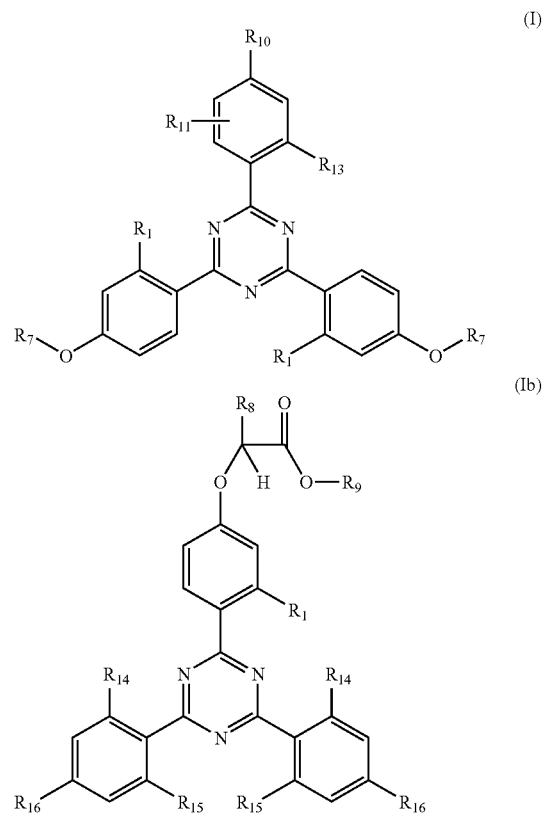

or an oligomeric or polymeric hydroxyphenyltriazine conforming to the formula (II)

$$-[A-L-D-L]_x-$$ (II)

in which
x is a number from 1 to 50;
A is a group of the formula (IIIb)

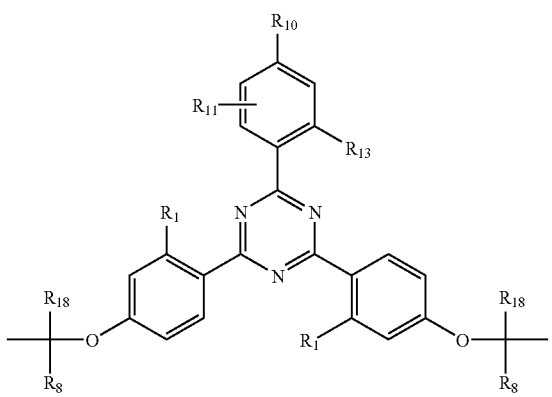

or has one of the meanings given for D, wherein formula (II) contains at least one A conforming to formula (IIIb);

D is a divalent residue containing 2 to 60 carbon atoms comprising an aliphatic, cycloaliphatic or aromatic hydrocarbon, or said aliphatic residue substituted by OH or interrupted by O or both substituted by OH and interrupted by O; and in case that D bonds to the carbon atom of L, D also comprises methylene or a direct bond;

L stands for an ester linkage group;

the $R_1$ are independently of each other H, $OR_7$ or OH, with the proviso that at least one of $R_1$ or $R_{13}$ is OH;

the $R_7$ are independently of each other hydrogen, $C_1$-$C_{12}$alkyl or a radical of formula (III)

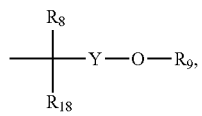
(III)

wherein in formula (I) at least one of the $R_7$ is a radical of formula (III);

$R_8$ is hydrogen, $C_1$-$C_{18}$alkyl; $C_5$-$C_{12}$cycloalkyl; $C_2$-$C_{18}$alkenyl; phenyl; $C_7$-$C_{11}$phenylalkyl; $C_7$-$C_{11}$alkylphenyl; $C_1$-$C_{18}$alkyl substituted by phenyl, OH, halogen; $C_1$-$C_{18}$alkoxy, $C_5$-$C_{12}$cycloalkoxy, $C_3$-$C_{18}$alkenyloxy or COOH;

Y is —CO— or $C_1$-$C_{12}$alkylene;

$R_9$, if Y is —CO—, is $C_{20}$-$C_{60}$ alkyl, $C_{20}$-$C_{60}$alkyl substituted by OH and/or interrupted by O, or is $C_{20}$-$C_{60}$alkenyl, or is a group of formula (IV)

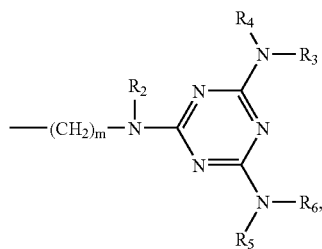
(IV)

wherein m is a number from 1 to 20;

$R_9$, if Y is alkylene, is $C_{20}$-$C_{60}$alkanoyl;

$R_2$, $R_3$, $R_4$, $R_5$ and $R_6$ are independently of each other hydrogen, $C_1$-$C_{38}$alkyl which is unsubstituted or substituted by hydroxy or $C_1$-$C_8$alkoxy; or
$C_1$-$C_{38}$alkyl which is interrupted by an oxygen atom or a $N(C_1$-$C_{18})$alkyl group;
phenyl or $C_7$-$C_{12}$phenylalkyl which are unsubstituted or substituted by hydroxy or $C_1$-$C_{18}$alkyl;

$R_{10}$ is hydrogen, $C_1$-$C_4$alkyl, Cl, phenyl or a group —$OR_7$;

$R_{11}$ is hydrogen or methyl;

$R_{13}$ is hydrogen, methyl, OH or $OR_7$;

$R_{14}$ and $R_{15}$ are independently hydrogen, $C_1$-$C_8$alkyl, Cl or a group $OR_7$;

$R_{16}$ is is hydrogen, $C_1$-$C_8$alkyl, Cl or phenyl;

$R_{18}$ is hydrogen or $C_1$-$C_8$alkyl.

Preferred are compounds of formula (I) or (II), wherein the $R_7$ are independently of each other hydrogen, $C_1$-$C_{12}$alkyl or a radical of formula (III)

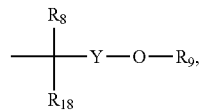
(III)

wherein in formula (I) at least one of the $R_7$ is a radical of formula (III);

$R_8$ is hydrogen or $C_1$-$C_8$alkyl;

Y is —CO— or $C_1$-$C_2$alkylene;

$R_9$, if Y is —CO—, is $C_{20}$-$C_{60}$ alkyl, $C_{20}$-$C_{60}$alkyl substituted by OH and/or interrupted by O, or is a group of formula (IV)

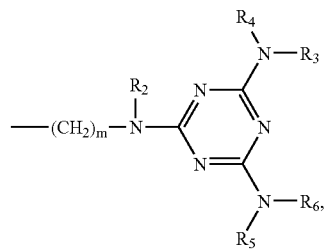
(IV)

wherein m is a number from 2 to 12;

$R_9$, if Y is alkylene, is $C_{20}$-$C_{60}$alkanoyl;

$R_2$, $R_3$, $R_4$, $R_5$ and $R_6$ are independently of each other hydrogen, $C_1$-$C_{18}$alkyl or
$C_4$-$C_{12}$hydroxyalkyl or $C_4$-$C_{12}$alkoxyalkyl;

$R_{10}$ is hydrogen or a group —$OR_7$;

$R_{11}$ and $R_{18}$ independently are hydrogen or methyl;

$R_{13}$ is hydrogen, OH or methyl.

Most preferably, the $R_1$ are OH;

the $R_7$ are hydrogen or methyl or a radical of formula (III)

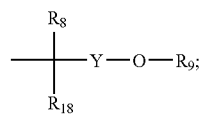
(III)

$R_8$ is hydrogen or $C_1$-$C_4$alkyl;

$R_{10}$ is hydrogen, methyl or a group —$OR_7$;

$R_{11}$ and $R_{18}$ are hydrogen;

$R_{13}$ is hydrogen, OH or methyl.

Terminal groups of the oligomer or polymer of formula (II) usually are
-L-D-COOR$_{12}$, -L-D-OR$_{12}$, or —OR$_{12}$ if bonded to A or D,
or -D-COOR$_{12}$, -D-OR$_{12}$, or —R$_{12}$ if bonded to L,
where $R_{12}$ is H or $C_1$-$C_8$alkyl.

The ester linkage group L is —COO— or —OCO—.

For example, the ester of formula (II) may conform to the formula (IIa)

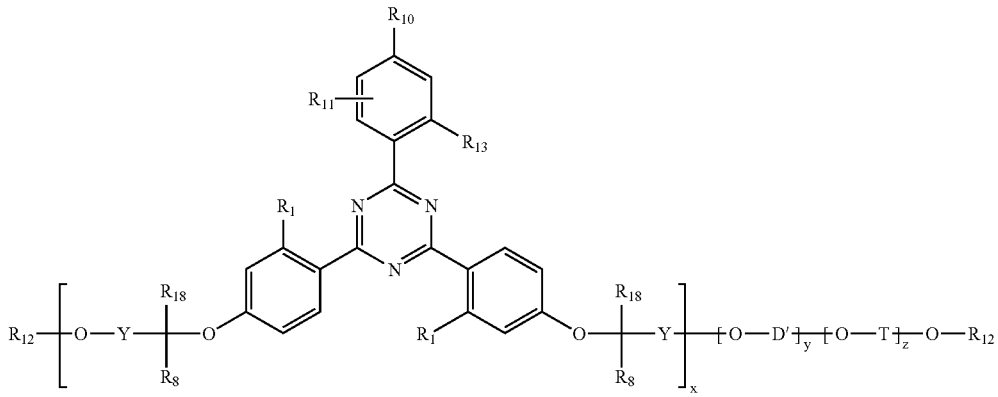

in which
x is a number from 1 to 20;
the number y is at least 1 and ranges from (x+z−1) to (x+z+1);
z is a number from 0 to 20; and
$R_{12}$ is hydrogen or $C_1$-$C_8$alkyl;
$R_{18}$ is hydrogen or $C_1$-$C_8$alkyl;
Y is —CO— or $C_1$-$C_{12}$alkylene;
if Y is —CO—, D' is $C_2$-$C_{38}$alkylene or $C_4$-$C_{60}$alkylene interrupted by O; and T is the divalent acyl residue of an aliphatic, cycloaliphatic or aromatic dicarboxylic acid of 2 to 12 carbon atoms;
if Y is alkylene, D' is the divalent acyl residue of an aliphatic, cycloaliphatic or aromatic dicarboxylic acid of 2 to 12 carbon atoms; and T is $C_2$-$C_{38}$alkylene or $C_4$-$C_{60}$alkylene interrupted by O;
and all other symbols are as defined above.

In the oligo- or polyester of formula (IIa), each of the divalent structural units identified by the indices x and z bond to the structural unit —O-D'- identified by the index y, and/or to an end group $R_{12}$ or $OR_{12}$.

The ester of formula (II) may also conform to the formula (IIb)

Most preferably, the moiety of formula

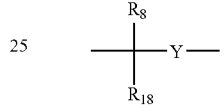

in formulae (IIa), (III) and (IIIb) is —CH(CH$_3$)—CO— or —CH$_2$CO— with Y being CO, or is —CH(CH$_3$)—CH$_2$— or —CH$_2$CH$_2$— with Y being methylene.

In a preferred embodiment, formula III conforms to the formula

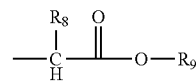

with $R_8$ being H or $C_1$-$C_8$alkyl, especially methyl.

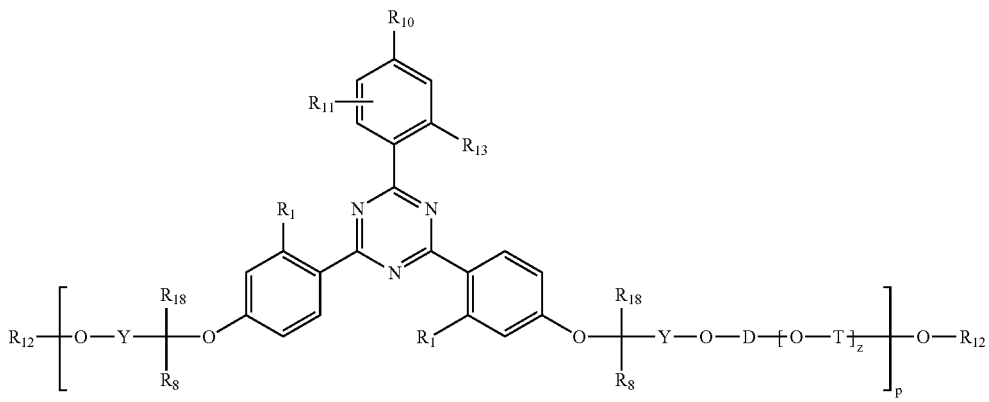

wherein
p ranges from 1 to 12, especially from 2 to 8;
z is 0 or 1; and all other symbols are as defined above.

Compounds of the formula (II) usually are of the type heteropolyester comprising two classes of structural units, one derived from dicarboxylic acids and the other from dioles. If in formula (II) the moiety L-A-L is a residue of a dicarboxylic acid, -D- is the residue of a divalent alcohol; if in formula (II) the moiety L-D-L is a residue of a dicarboxylic acid, -A- is the residue of a divalent alcohol.

L-D-L as a divalent acyl residue conforms to the formula —OCO-D-COO—, D' or T as a divalent acyl residue conform to the formula —CO-T'—CO—, wherein D or T' is, for example, a direct bond, $C_1$-$C_{60}$alkylene, $C_2$-$C_{10}$alkenylene, phenylene, naphthylene, $C_5$-$C_8$cycloalkylene, $C_2$-$C_4$alkylene or alkenylene interrupted by O or cyclohexylene or phenylene, $C_1$-$C_{12}$alkylene substituted by OH. More preferred D or T' in this meaning are phenylene, cyclohexylene, $C_2$-$C_{10}$alkylene, or $C_2$-$C_{10}$alkylene substituted by OH.

D' or T as a diol residue conform to the formula —O-T'-O—; D or T' in this meaning are, for example, $C_2$-$C_{60}$alkylene, $C_2$-$C_{10}$alkenylene, $C_5$-$C_8$cycloalkylene, $C_4$-$C_{60}$alkylene or alkenylene interrupted by O, cyclohexylene and/or phenylene. More preferred D or T' in this meaning are $C_2$-$C_{24}$alkylene, or $C_4$-$C_{60}$alkylene interrupted by O.

In compounds of the formula (II), x is preferably from the range 2-50, more preferably from the range 2-20, especially 4-12. In compounds of the formula (IIa), each of x and y are preferably from the range 2-16, more preferably from the range 4-12; z is preferably ranging from 0-12. Of specific technical interest are compounds of the formula (IIa) wherein z is 0.

Oligomeric or polymeric esters of the invention such as those of formula II usually have a molecular weight within the range 1000 to 50000 g/mol, more preferably 1500 to 20000 g/mol, most preferably 2000 to 10000 g/mol (number average Mn as determined by gel permeation chromatography GPC).

Of specific value is a hydroxyphenyltriazine of formula (I), (Ia) or (Ib)

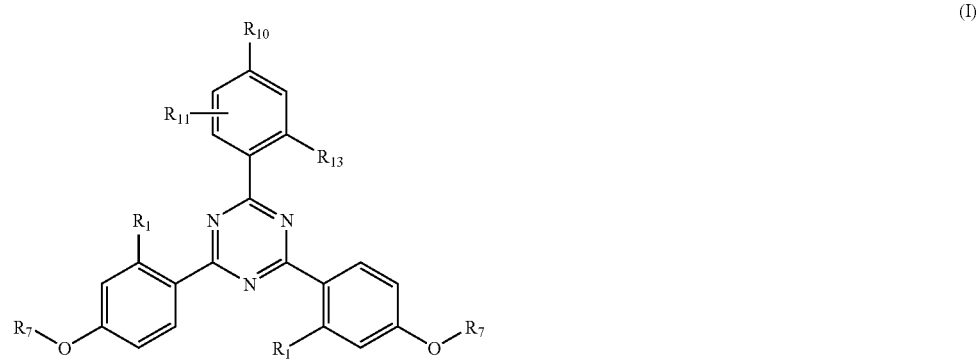

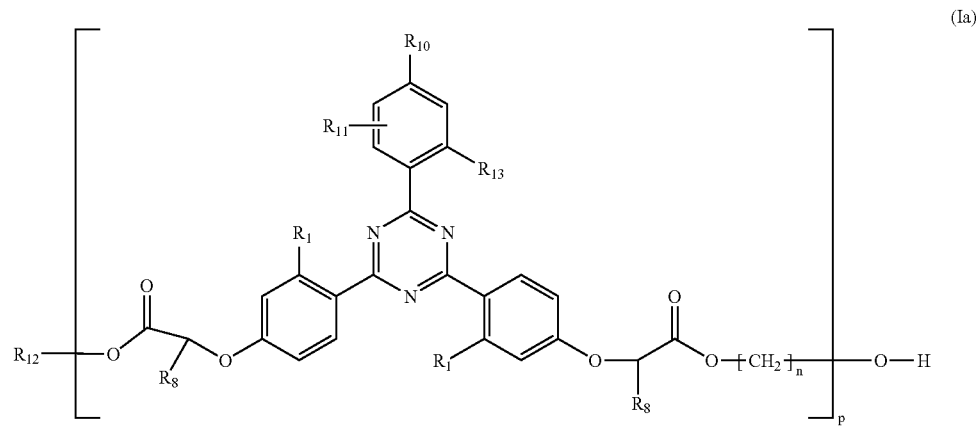

-continued

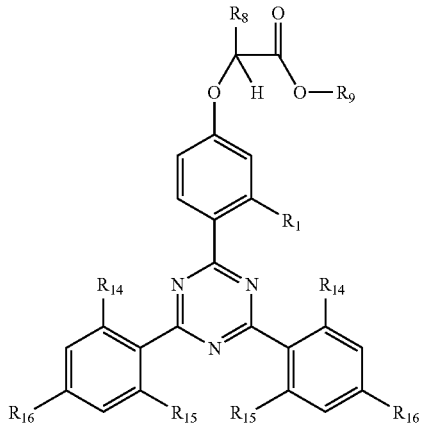

in which
the $R_1$ are independently of each other H, $OR_7$ or OH, with the proviso that at least one of $R_1$ or $R_{13}$ is OH;
the $R_7$ are independently of each other hydrogen, $C_1$-$C_{12}$alkyl or a radical of formula III

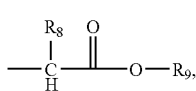

wherein in formula I at least one of the $R_7$ is a radical of formula III;
$R_8$ is hydrogen, $C_1$-$C_{18}$alkyl; $C_5$-$C_{12}$cycloalkyl; $C_2$-$C_{18}$alkenyl; phenyl; $C_7$-$C_{11}$phenylalkyl; $C_7$-$C_{11}$alkylphenyl; $C_1$-$C_{18}$alkyl substituted by phenyl, OH, halogen; $C_1$-$C_{18}$alkoxy, $C_5$-$C_{12}$cycloalkoxy, $C_3$-$C_{18}$alkenyloxy or COOH;
$R_9$, is $C_{20}$-$C_{60}$ alkyl, $C_{20}$-$C_{60}$alkyl which is substituted in ω position with a OH group or
$C_{20}$-$C_{60}$alkenyl or a group of formula (IV)

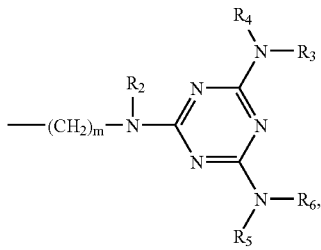

wherein
m is a number from 1 to 20;
$R_2$, $R_3$, $R_4$, $R_5$ and $R_6$ are independently of each other hydrogen, $C_1$-$C_{38}$alkyl which is unsubstituted or substituted by hydroxy or $C_1$-$C_8$alkoxy; or
$C_1$-$C_{38}$alkyl which is interrupted by an oxygen atom or a $N(C_1$-$C_{18})$alkyl group;
phenyl or $C_7$-$C_{12}$phenylalkyl which are unsubstituted or substituted by hydroxy or $C_1$-$C_8$alkyl;

n is a number-from 1 to 38;
p is a number from 2 to 20; and
$R_{10}$ is hydrogen, $C_1$-$C_4$alkyl, Cl, phenyl or a group —$OR_7$;
$R_{11}$ is hydrogen or methyl;
$R_{12}$ is hydrogen, methyl or ethyl;
$R_{13}$ is hydrogen, methyl, OH or a group $OR_7$;
$R_{14}$ and $R_{15}$ are independently hydrogen, $C_1$-$C_8$alkyl, Cl or a group $OR_7$; and
$R_{16}$ is is hydrogen, $C_1$-$C_8$alkyl, Cl or phenyl.

Alkylphenyl is alkyl-substituted phenyl; $C_7$-$C_{14}$alkylphenyl embraces examples such as methylphenyl (tolyl), dimethylphenyl (xylyl), trimethylphenyl (mesityl), ethylphenyl, propylphenyl, butylphenyl, dibutylphenyl, pentylphenyl, hexylphenyl, heptylphenyl and octylphenyl.

Phenylalkyl is phenyl-substituted alkyl; $C_7$-$C_{11}$phenylalkyl embraces examples such as benzyl, α-methylbenzyl, α-ethylbenzyl, α,α-dimethylbenzyl, phenylethyl, phenylpropyl, phenylbutyl and phenylpentyl.

Alkyl interrupted by O, NH, N($C_1$-$C_{12}$)alkyl can generally comprise one or more nonadjacent heteroatoms. Preferably, a carbon atom of the alkyl chain bonds to not more than 1 heteroatom.

Within the scope of the stated definitions, the alkyl radicals are branched or unbranched alkyl such as methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl and octadecyl.

Examples for the $C_{20}$-$C_{60}$alkyl radicals in the definition of $R_9$ are icosyl, henicosyl, docosyl, tricosyl, pentacosyl, heptacosyl, nonacosyl, triacontyl, dotriacontyl, tetracontyl, pentacontyl and hexacontyl.

Within the scope of the stated definitions, the alkenyl radicals include allyl, isopropenyl, 2-butenyl, 3-butenyl, isobutenyl, n-penta-2,4-dienyl, 3-methyl-but-2-enyl; n-oct-2-enyl, n-dodec-2-enyl, isododecenyl, n-octadec-2-enyl and n-octadec-4-enyl.

Preferred are compounds of the formula (I) or (II), especially of the formula (II).

Preferred is a compound wherein $R_8$ is $C_1$-$C_{18}$alkyl more preferably $C_1$-$C_8$alkyl, in particular methyl.

Preferred is $R_{18}$ as hydrogen or methyl, especially hydrogen.

$R_9$ as $C_{20}$-$C_{60}$alkyl substituted by OH preferably carries only one OH group in ω position. Preferred is a compound wherein $R_9$ is $C_{20}$-$C_{60}$alkyl, more preferred $C_{26}$-$C_{52}$alkyl and in particular $R_9$ is a mixture of alkyl with a range from 20 to 40 carbon atoms the mean value being around 32 carbon atoms.

The high alkyl groups of $R_9$ may also have a certain molecular distribution around their main component. Ranges may for example be from 22-26, 28-32 or 34-38 C-atoms. It is however also possible that broader ranges are used such as for example from 20 to 40, from 30 to 50 or from 40 to 60 carbon atoms.

Since the educts for preparing a compound of formula (I), (Ia) or (Ib) are commercial products they may vary within certain specifications. This is particularly the case for high molecular weight alcohols from which the $R_9$ groups are derived, when $R_9$ is $C_{20}$-$C_{60}$alkyl.

Commercially available alcohols may also contain small amounts of alkyl chains below $C_{20}$. Therefore mixtures of compounds wherein $R_9$ is a mixture containing up to 10% of alkyl chains below 20 carbon atoms and 90 to 100% of alkyl chains between 20 and 60, particularly between 20 and 40 carbon atoms are also subject of the invention. Percentage is weight percent, based on the total mixture.

If $R_9$ is a group of formula (IV), $R_2$ is preferably hydrogen or $C_1$-$C_4$alkyl $R_3$, $R_4$, $R_5$ and $R_6$ are preferably hydrogen or $C_1$-$C_{38}$alkyl, more preferably $C_4$-$C_{24}$alkyl and in particular $C_4$-$C_{12}$alkyl.

n is preferably 2-24, more preferably 4-16 and most preferably 4-12.

p is preferably 2-12 and more preferably 2-8.

The compounds of formula I, (Ia), (Ib) and (II) or precursors thereof can be prepared in analogy to one of the methods indicated in EP-A-434 608, one of the publications specified at the outset, or in the publication by H. Brunetti and C. E. Lüthi, Helv. Chim. Acta 55, 1566 (1972), by Friedel-Crafts addition of halotriazines with corresponding phenols; see also U.S. Pat. No. 3,118,887 and EP-A-165608. This can be followed by a further, conventional reaction to give compounds of the formula I in which $R_7$ is other than hydrogen; such reactions and methods are described, for example, in EP-A-434 608, page 15, line 11, to page 17, line 1. Further examples of the preparation are given in GB 2337049.

(Poly)esters of formula (Ia), (II) or (IIa) are advantageously prepared starting from tris-aryl-triazines containing 2 carboxylic acid groups or suitable derivatives thereof such as acid chloride, anhydride or especially ester groups, or, alternatively, 2 reactable, preferably primary, OH groups. Such educts or their homologues are described, inter alia, in U.S. Pat. Nos. 4,826,978, 5,736,597 (see e.g. columns 11-13), U.S. Pat. Nos. 5,686,233, 5,959,008 (see e.g. col. 30, line 35, until col. 31, line 11). Further educts of the same type, e.g. aliphatic, cycloaliphatic or aromatic dicarboxylic acids or derivatives thereof, or dialcohols, may be added. For esterification, the dicarboxylic educts are preferably reacted according to methods known in the art with suitable amounts, e.g. 0.9-1.1 mol per mol dicarboxyl or equimolar amounts, of a diol HO-D-OH, with or without additional dicarboxylic compounds present; diol educts are correspondingly reacted with dicarboxylic acids, anhydrides, acid chlorides or preferably esters e.g. of formula $R_{12}$—O-D-O—$R_{12}$. Preferred dicarboxylic acid educts include those based on oxalic, malonic, maleic, malic, fumaric, succinic, glutaric, adipinic, pimelic, suberic, azelaic, sebacic, phthalic, isophthalic, terephthalic, cyclohexyl dicarboxylic, glutaconic, itaconic, tartaric acid; preferred diols include glycol, glycerine, various polyethylene glycoles, or α,ω-dihydroxyalkanes of various chain lengths such as butanediol, pentanediol, hexanediol, heptanediol, octanediol, nonanediol, decanediol, undecanediol, dodecanediol, tridecanediol, pentadecanediol, octadecanediol, elcosanediol, and mixtures thereof. Reaction can be carried out with or without addition of further components such as solvents (e.g. aliphatic alcohols, ethers, aromatic hydrocarbons or halogenated hydrocarbons such as chlorobenzene, or solvent mixtures) or catalysts, e.g. transesterification catalysts such as mineral or organic (Lewis or Broensted-type) acids or bases. In case that no additional solvent is used, an educt such as the diol or a suitable ester of a dicarboxylic acid may be used in excess and serve simultaneously as a solvent. Temperature and pressure are usually not critical, thus, the reaction often is carried out at temperatures in the range −5° C. to 200° C., e.g. between 10 and 170° C., and pressure close to 1 atmosphere, e.g. $10^4$ to about $10^6$ Pa, with or without presence of oxygen, e.g. under nitrogen or argon.

Present invention also pertains to an oligoester or polyester which is obtained by reacting a tris-aryl-triazine of the formula V

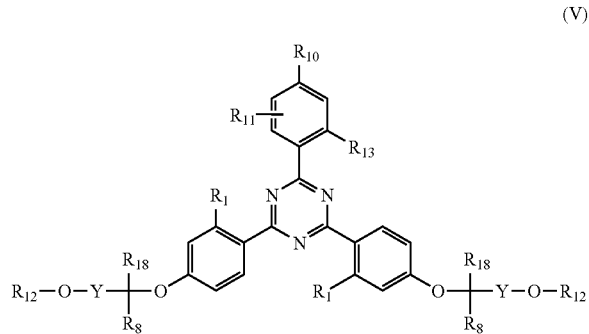

(V)

wherein all symbols are as defined for formula (IIa) above, provided that $R_{12}$ is hydrogen in case that Y is alkylene,
if Y is —CO—, with a diol HO-D-OH, optionally in presence of a compound of the formula $R_{12}$—O-T-O—$R_{12}$; and
if Y is alkylene, with a diacid or diester $R_{12}$—O-T-O—$R_{12}$, optionally in presence of a diol of the formula HO-T-OH.

Present invention also pertains to a composition protected against the permeation of ultraviolet radiation comprising
(a) an organic polymer material, e.g. a synthetic thermoplastic polymer, and
(b) at least one compound of formula (I), (II) or (Ib) or a mixture thereof.

A further subject of the invention is a plastic container or film which protects against the deleterious effects of ultraviolet radiation which comprise
(a) a clear or lightly colored plastic, and
(b) at least one compound of formula (I), (II) or (Ib) or a mixture thereof.

Definitions and preferences for the compounds of formula (I), (II), (Ia) and (Ib) have been already given and apply also for this subject of the invention.

The compounds are useful for many kinds of plastic materials from which containers, sheets, films and woven or nonwoven fabrics can be made. Examples are given below.

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EM), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates (PMMA), polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 416, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polyketones.

21. Polysulfones, polyether sulfones and polyether ketones.

22. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Preferred is a is a polyolefin, a polyester, a polyvinylalcohol, a polyvinylacetate, a polycarbonate, a polyamide, an acrylic (co)polymer, or acryl-butadiene-styrene terpolymer (ABS); especially a polyolefin, a polyester, a polyvinylalcohol, a polyvinylacetate or a polycarbonate. Preferably, the organic polymer material is a plastic container or film or sheet wherein the plastic material is transparent, for instance clear, or lightly colored.

More preferred materials for films or plastic containers are a polyolefin, a polyester, a polyvinylalcohol, a polyvinylacetate or a polycarbonate; most preferred are polyethyleneterephthalate (PET) and polyolefins, in particular (PE), polyethylene, (LDPE), low density polyethylene, linear low density polyethylene (LLDPE), (VLDPE) and (ULDPE). More preferred materials for sheets are polycarbonate, a polyamide, a polyacryl, or transparent ABS, especially polycarbonate.

The present UV absorbers may also be incorporated into optical lenses or glasses, such as acryl glasses, or coatings thereon. Preferred materials for optical lenses and glasses, e.g. for sunglasses, are acrylics or polycarbonate, especially polymethyl methacrylate (PMMA).

Most advantageously, the composition of the invention is a plastic container or film used as a food packaging material.

Preferably the thickness of the film is from 10μ to 200μ, more preferably from 20μ to 80μ and in particular from 20μ to 60μ and of the plastic container from 200μ to 1000μ. Preferably, the thickness of the sheet may vary between about 0.5 to 8 mm, e.g. for solid sheets, to about 3 to 100 mm, e.g. for twin or multiple wall sheets.

Preferably, the compound of formula (I), (II), (IIa), (Ia) or (Ib) is present in an amount of from 0.005% to 10%, more preferably of from 0.05% to 4%, and most preferably of from 0.1% to 2.5%, based on the weight of the plastic material.

Alongside the stabilizer of the invention, the plastic material of the invention may also include other stabilizers or other additives, such as a phenolic antioxidant, a sterically hindered amine and/or a phosphite or phosphonite.

The plastic container or film may also additionally contain an iron based additive as oxygen absorber.

Examples for further stabilizers and additives are given below.

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4- methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O—, N— and S-benzyl compounds, for example 3,5,3',5'-tetra-tert-butyl-4,4'-dihydroxydi-benzyl ether, octadecyl-4-hydroxy-3,5-dimethylbenzylmercaptoacetate, tridecyl-4-hydroxy-3,5-di-tert-butylbenzylmercaptoacetate, tris (3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxy-benzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane.

1.15. Esters of β-(3.5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl)trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl] propionyloxy)ethyl]oxamide (Naugard®XL-1 supplied by Uniroyal).

1.18. Ascorbic Acid (Vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino] ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- and dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-($\alpha,\alpha$-dimethylbenzyl)-2'-hydroxyphenyl)benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—COO—$CH_2CH_2$—]$_2$ where R=3'-tert-butyl-4'-hydroxy-5'-2H-benzotriazol-2-ylphenyl, 2-[2'-hydroxy-3'-($\alpha,\alpha$-dimethylbenzyl)-5'-(1,1,3,3-tetramethylbutyl)-phenyl]benzotriazole; 2-[2'-hydroxy-3'-(1,1,3,3-tetramethylbutyl)-5'-($\alpha,\alpha$-dimethylbenzyl)-phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxy-cinnamate, butyl $\alpha$-cyano-$\beta$-methyl-p-methoxycinnamate, methyl $\alpha$-carbomethoxy-p-methoxycinnamate and N-($\beta$-carbomethoxy-$\beta$-cyanovinyl)-2-methylindoline.

2.5. Nickel compounds, for example nickel complexes of 2,2'-thio-bis-[4-(1,1,3,3-tetramethyl-butyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris (2,2,6,6-tetramethyl-4-piperidyl)nitrilotriacetate, tetrakis(2, 2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4,5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro4,6-bis(4-n-butylamino-2,2,6,6-tetramethylpiperidyl)-1,3,5-triazine and 1,2-bis(3-aminopropylamino)
ethane, the condensate of 2-chloro4,6-di-(4-n-butylamino-
1,2,2,6,6-pentamethylpiperidyl)-1,3,5-triazine and 1,2-bis-
(3-aminopropylamino)ethane, 8-acetyl-3-dodecyl-7,7,9,9-
tetramethyl-1,3,8-triazaspiro[4,5]decane-2,4-dione,
3-dodecyl-1-(2,2,6,6-tetramethyl-4-piperidyl)pyrrolidin-2,
5-dione, 3-dodecyl-1-(1,2,2,6,6-pentamethyl-4-piperidyl)
pyrrolidine-2,5-dione, a mixture of 4-hexadecyloxy- and
4-stearyloxy-2,2,6,6-tetramethylpiperidine, a condensation
product of N,N'-bis(2,2,6,6-tetramethyl-4-piperidyl)hexam-
ethylenediamine and 4-cyclohexylamino-2,6-dichloro-1,3,
5-triazine, a condensation product of 1,2-bis(3-aminopropy-
lamino)ethane and 2,4,6-trichloro-1,3,5-triazine as well as
4-butylamino-2,2,6,6-tetramethylpiperidine (CAS Reg. No.
[136504-96-6]); N-(2,2,6,6-tetramethyl-4-piperidyl)-n-
dodecylsuccinimid, N-(1,2,2,6,6-pentamethyl-4-piperidyl)-
n-dodecylsuccinimid, 2-undecyl-7,7,9,9-tetramethyl-1-oxa-
3,8-diaza-4-oxo-spiro[4,5]decane, a reaction product of 7,7,
9,9-tetramethyl-2-cycloundecyl-1-oxa-3,8-diaza-4-oxospiro
[4,5]decane und epichlorohydrin, 1,1-bis(1,2,2,6,6-pentam-
ethyl-4-piperidyloxycarbonyl)-2-(4-methoxyphenyl)ethene,
N,N'-bis-formyl-N,N'-bis(2,2,6,6-tetramethyl-4-piperidyl)
hexamethylenediamine, diester of 4-methoxy-methylene-
malonic acid with 1,2,2,6,6-pentamethyl-4-hydroxypiperi-
dine, poly[methylpropyl-3-oxy-4-(2,2,6,6-tetramethyl-4-
piperidyl)]siloxane, reaction product of maleic acid
anhydride-α-olefin-copolymer with 2,2,6,6-tetramethyl-4-
aminopiperidine or 1,2,2,6,6-pentamethyl-4-aminopiperi-
dine. Of special importance, especially for use in agricul-
tural or greenhouse films, are bis(2,2,6,6-tetramethyl-4-piperidyl)sebacate;
bis(1,2,2,6,6-pentamethyl-4-piperidyl)sebacate;
the condensate of 1-(2-hydroxyethyl)-2,2,6,6-tetramethyl-4-
  hydroxypiperidine and succinic acid (CAS-No. 65447-
  77-0);
N,N',N'',N'''-Tetrakis(4,6-bis(butyl-(N-methyl-2,2,6,6-tet-
  ramethylpiperidin-4-yl)amino)triazin-2-yl)-4,7-diazade-
  cane-1,10-diamine (CAS-No. 106990-43-6);

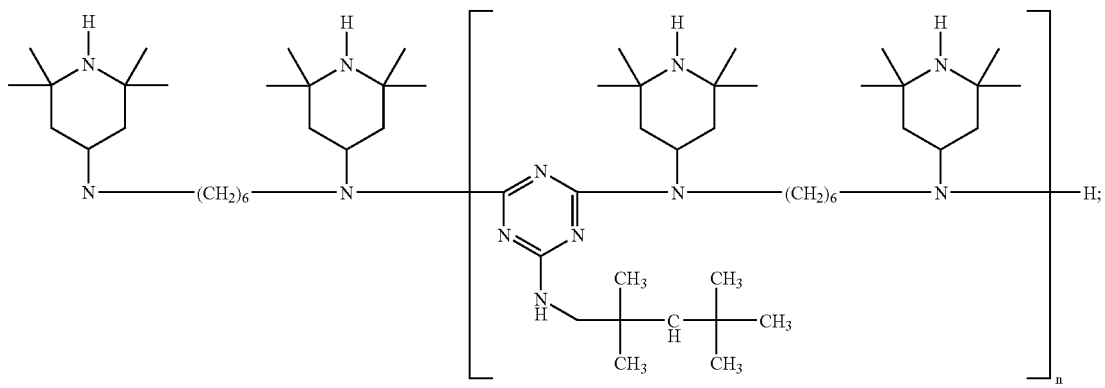

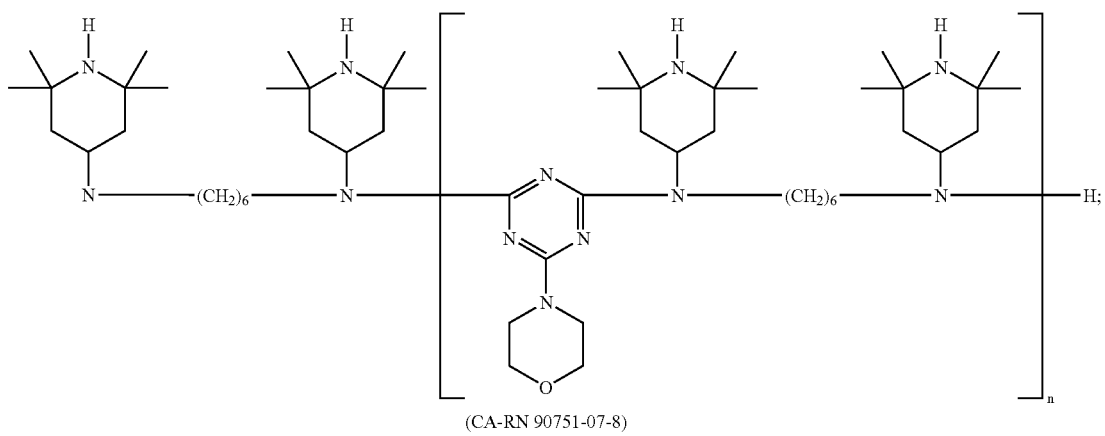

(CA-RN 90751-07-8)

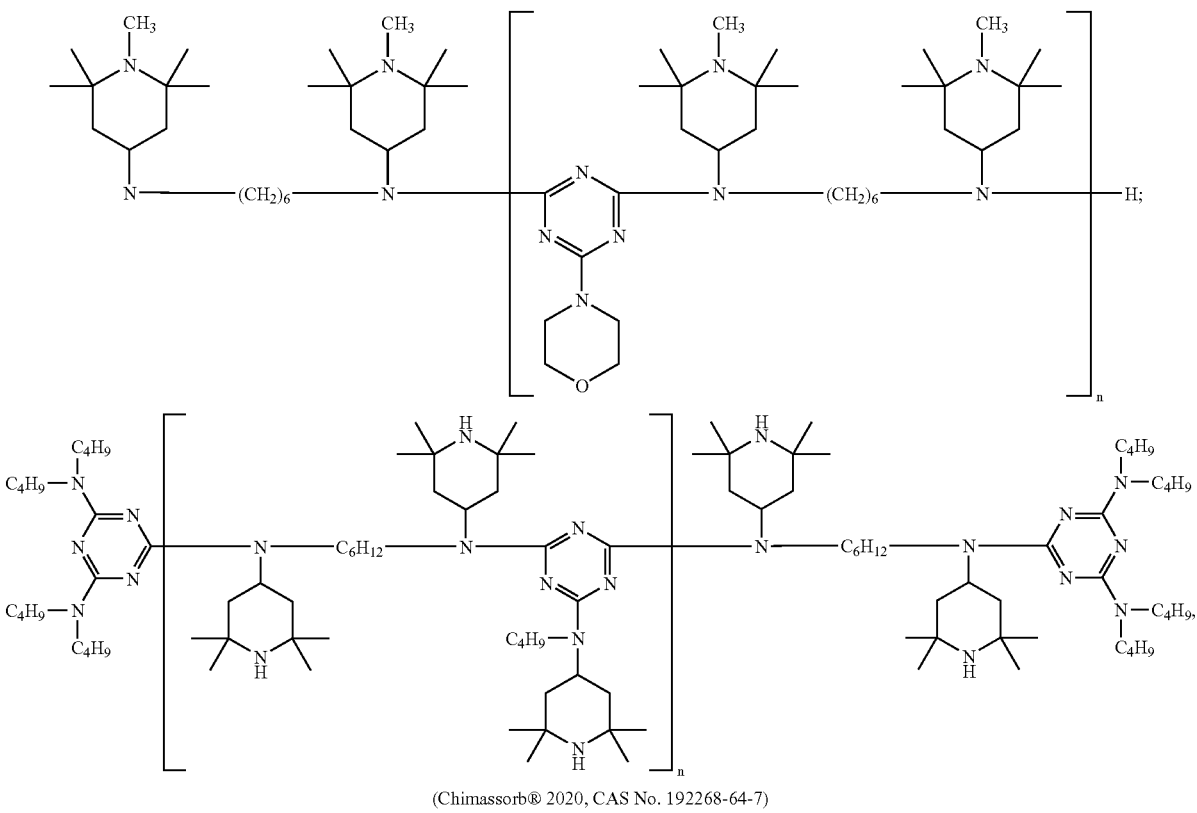
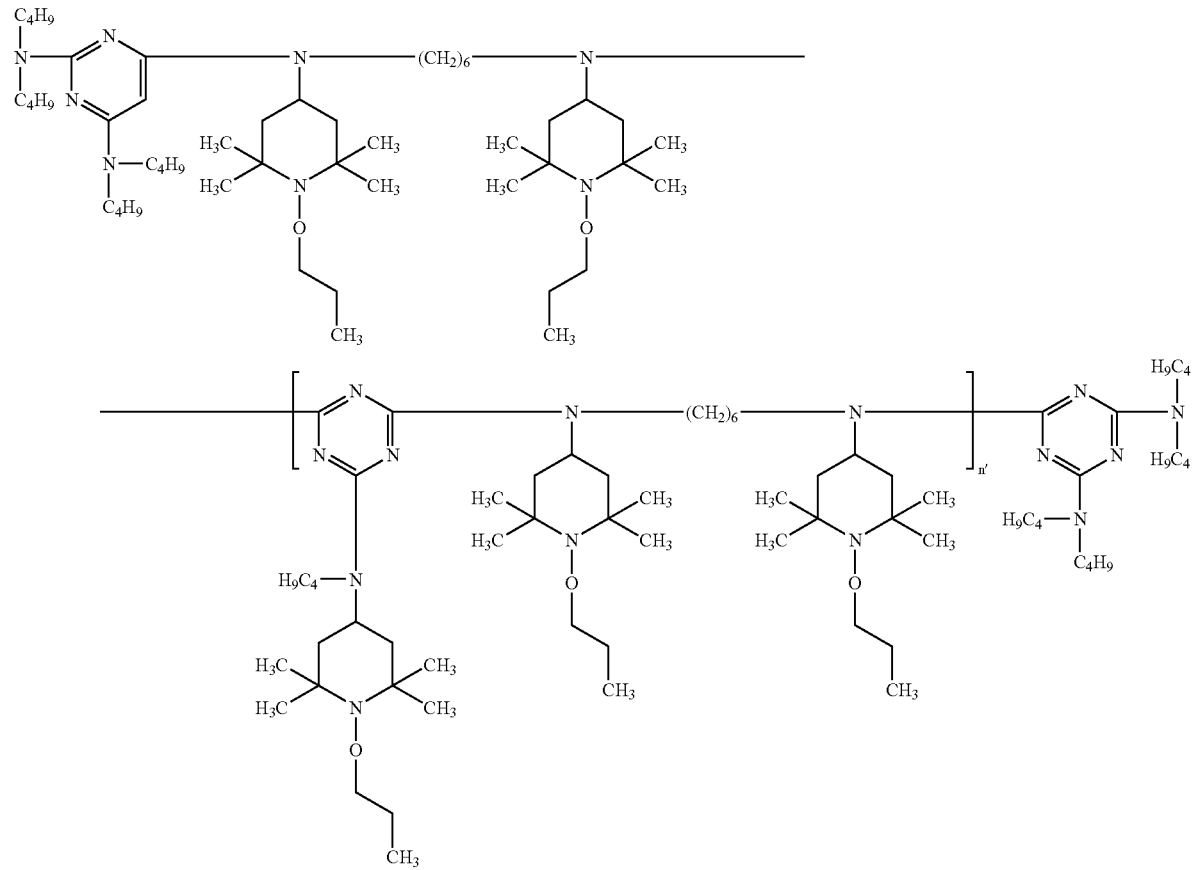

where n or n' is mainly from the range 3-5; or mixtures of these compounds.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo[triethyltris(3,3',5,5'-tetra-tert-butyl-1,1'-biphenyl-2,2'-diyl)phosphite], 2-ethylhexyl (3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

Especially preferred are the following phosphites:
Tris(2,4-di-tert-butylphenyl) phosphite (Irgafos®168, Ciba-Geigy), tris(nonylphenyl) phosphite,

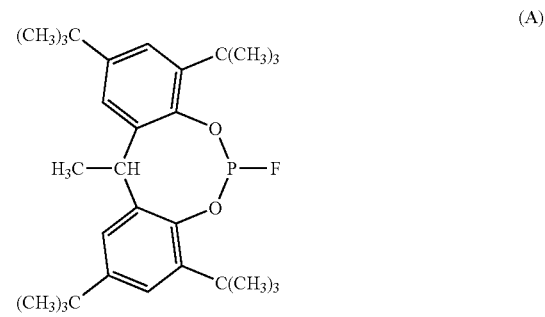
(A)

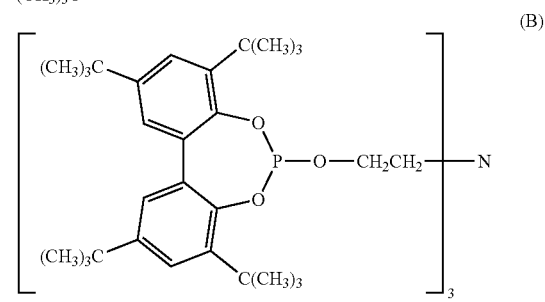
(B)

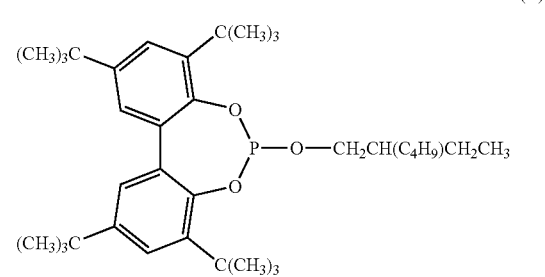
(C)

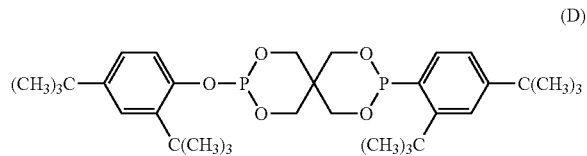
(D)

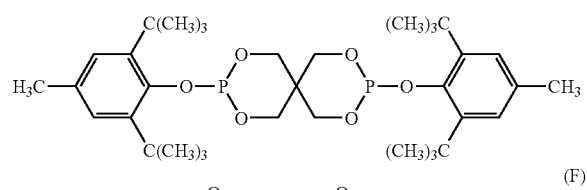
(E)

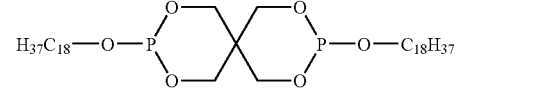
(F)

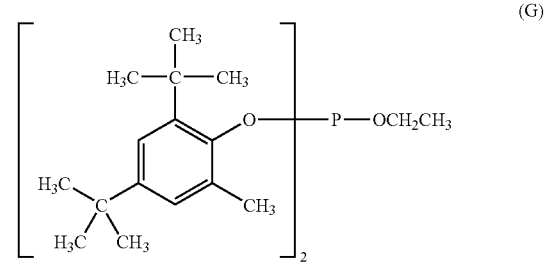
(G)

5. Hydroxylamines, for example, N,N-dibenzylhydroxylamine, N,N-diethylhydroxylamine, N,N-dioctylhydroxylamine, N, N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers). Especially preferred are 1,3:2,4-bis(3',4'-dimethylbenzylidene)sorbitol, 1,3:2,4-di(paramethyldibenzylidene)sorbitol, und 1,3:2,4-di(benzylidene)sorbitol.

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, oxygen absorbers, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The nature and amount of the further stabilizers added are determined by the nature of the substrate to be stabilized and its intended use; in many cases from 0.01 to 5% by weight is used, based on the polymer to be stabilized.

Preferably sterically hindered amines such as for example mentioned under item 2.6 are additionally present. In agricultural or greenhouse films, good results are achieved with further addition of a metal oxide or hydroxide such as ZnO, MgO or $Mg(OH)_2$ and/or a hydrotalcite. Advantageously, polyolefines further contain a metal carboxylate such as Ca- or Zn-stearate.

The additives of the invention and optional further components may be added to the polymer material individually or mixed with one another. If desired, the individual components can be mixed with one another before incorporation into the polymer for example by dry blending, compaction or in the melt.

The incorporation of the additives of the invention and optional further components into the polymer is carried out by known methods such as dry blending in the form of a powder, or wet mixing in the form of solutions, dispersions or suspensions for example in an inert solvent, water or oil. The additives of the invention and optional further additives may be incorporated, for example, before or after molding or also by applying the dissolved or dispersed additive or additive mixture to the polymer material, with or without subsequent evaporation of the solvent or the suspension/dispersion agent. They may be added directly into the processing apparatus (e.g. extruders, internal mixers, etc), e.g. as a dry mixture or powder or as solution or dispersion or suspension or melt.

The incorporation can be carried out in any heatable container equipped with a stirrer, e.g. in a closed apparatus such as a kneader, mixer or stirred vessel. The incorporation is preferably carried out in an extruder or in a kneader. It is immaterial whether processing takes place in an inert atmosphere or in the presence of oxygen.

The addition of the additive or additive blend to the polymer can be carried out in all customary mixing machines in which the polymer is melted and mixed with the additives. Suitable machines are known to those skilled in the art. They are predominantly mixers, kneaders and extruders.

The process is preferably carried out in an extruder by introducing the additive during processing.

Particularly preferred processing machines are single-screw extruders, contrarotating and corotating twin-screw extruders, planetary-gear extruders, ring extruders or cokneaders. It is also possible to use processing machines provided with at least one gas removal compartment to which a vacuum can be applied.

Suitable extruders and kneaders are described, for example, in *Handbuch der Kunststoffex-trusion, Vol. 1 Grundlagen,* Editors F. Hensen, W Knappe, H. Potente, 1989, pp. 3-7, ISBN:3-446-14339-4 (*Vol. 2 Extrusionsanlagen* 1986, ISBN 3-446-14329-7).

For example, the screw length is 1-60 screw diameters, preferably 35-48 screw diameters. The rotational speed of the screw is preferably 10-600 rotations per minute (rpm), very particularly preferably 25-300 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

If a plurality of components are added, these can be premixed or added individually. The additives of the invention and optional further additives can also be sprayed onto the polymer material. They are able to dilute other additives (for example the conventional additives indicated above) or their melts so that they can be sprayed also together with these additives onto the material. Addition by spraying during the deactivation of the polymerization catalysts is particularly advantageous; in this case, the steam evolved may be used for deactivation of the catalyst. In the case of spherically polymerized polyolefins it may, for example, be advantageous to apply the additives of the invention, optionally together with other additives, by spraying.

The additives of the invention and optional further additives can also be added to the polymer in the form of a masterbatch ("concentrate") which contains the components in a concentration of, for example, about 1% to about 40% and preferably 2% to about 20% by weight incorporated in a polymer. The polymer must not be necessarily of identical structure than the polymer where the additives are added finally. In such operations, the polymer can be used in the form of powder, granules, solutions, suspensions or in the form of latices.

Incorporation can take place prior to or during the shaping operation, or by applying the dissolved or dispersed compound to the polymer, with or without subsequent evaporation of the solvent. In the case of elastomers, these can also be stabilized as latices. A further possibility for incorporating the additives of the invention into polymers is to add them before, during or directly after the polymerization of the corresponding monomers or prior to crosslinking. In this context the additive of the invention can be added as it is or else in encapsulated form (for example in waxes, oils or polymers).

In a specific embodiment the plastic container or film or sheet is a multilayer construction of between 2 and 7 polymer layers containing a compound of formula (I), (II) or (Ib) or a mixture thereof in at least 1 layer. In this case, a polymer composition of the invention containing a relatively large amount of the compatible hydroxyphenyltriazine stabilizer, for example 1-15% by weight, is applied in a thin layer (e.g. 5-100μ) to a shaped article made from a polymer containing little or no stabilizer of the invention. Application can be made at the same time as the shaping of the base article, for example by coextrusion. Alternatively, application can be made to the base article after it has been shaped, for example by lamination with a film or by coating with a solution. The external layer or layers of the finished article has or have the function of a UV filter which protects the interior of the article and/or inner layer(s) against UV light.

Still a further subject of the invention is the use of a compound of formula (I), (II) or (Ib) or a mixture thereof which is incorporated into a plastic container or film or sheet, for content protection of greenhouses or packaged foodstuffs, beverages, pharmaceuticals, cosmetics or personal care products.

Content protection of packaged foodstuffs, beverages, pharmaceuticals, cosmetics or personal care products is preferred.

The following examples illustrate the invention. All parts or percentages, in the examples as in the remainder of the description and in the claims, are by weight, unless stated otherwise. Room temperature denotes a temperature in the range 20-30° C., unless stated otherwise. Data given for elemental analysis are in % by weight calculated (cal) or experimentally measured (exp) for the elements C, H and N. In the examples, the following abbreviations are used:

% w/w percent by weight;

l liter;

m.p. melting point or range;

PP polypropylene;

LDPE low density polyethylene;

DSC differential scan calorimetry;

NMR nuclear magnetic resonance (of $^1$H, if not otherwise indicated);

$\epsilon$ at $\lambda_{max}$ molar extinction coefficient (1 mol$^{-1}$ cm$^{-1}$) at long wavelength UV absorption maximum;

Mn number average of molecular mass (g/mol) as determined by GPC;

GPC gel permeation chromatography;

PDI polydispersity (ratio of mass and number average of molecular weight).

In the following examples, the molecular weight parameters (Mn, Mw, PDI) are determined by GPC (Gel Permeation Chromatography). The GPC measurements are carried out on a Perkin Elmer LC 50 liquid chromatograph equipped with a reflective index Perkin Elmer LC 30 and the data are calculated by using a Perkin Elmer software (TurboSEC). All GPC measurements are carried out by using 0.02 M di-ethanol-amine solution in chromatographic grade tetrahydrofuran (THF) as solvent at 45° C. The columns used are PLGEL (Polymer Laboratories) 300 mm×7.5 mm, stationary phase 3 mm Mixed E, supplied by Polymer Laboratories. Polystyrene standards are used for the calibration curve. Visual melting points and melting ranges are measured by using a Gallenkamp equipment. The extinction coefficients (e) are calculated by recording the UV spectra of the products in methylene chloride or toluene solutions on a Perkin Elmer Lambda 2S spectrophotometer.

A: PREPARATION EXAMPLES

Example A1

Synthesis of compound 101 of formula

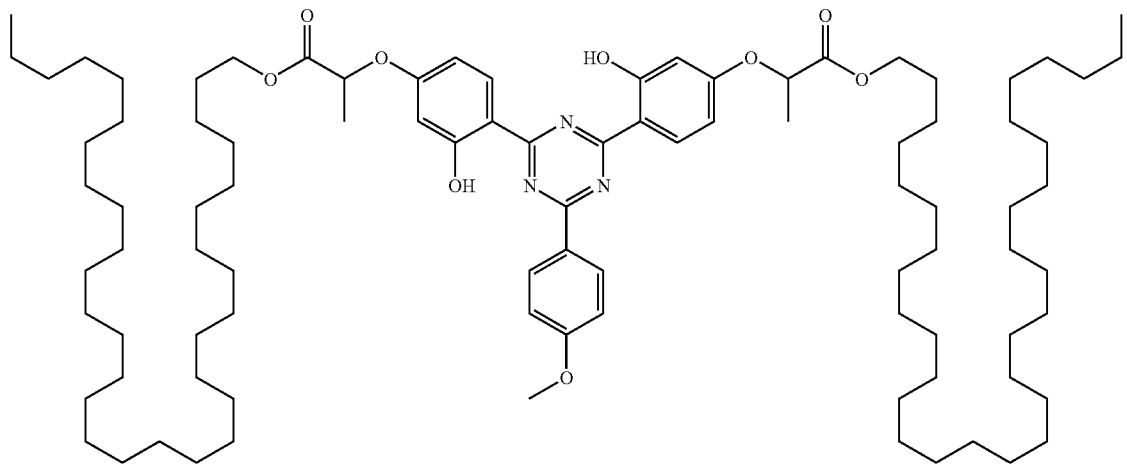

a) Synthesis of the Intermediate

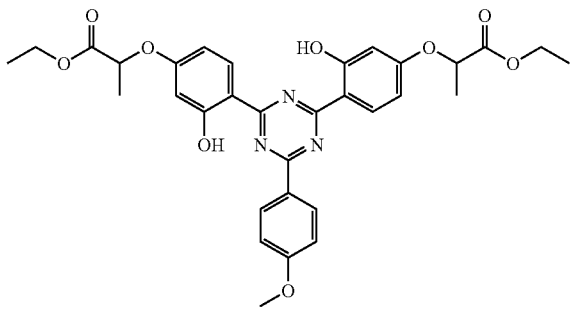

A solution of 86 g 2-(4-methoxyphenyl)-4,6-bis-resorcinol-1,3,5-triazine and 23.5 g sodium methylate in 300 ml methanol is heated to 50° C. 82.8 g Methyl-2-bromopropionate is added dropwise over 30 minutes. The mixture is then heated under reflux for 2 hours. The methanol is distilled off, a suspension of 55.3 g potassium carbonate in 300 ml xylene added and to heated under reflux for 12 hours. 55 g Potassium carbonate and 8.3 g methyl 2-bromopropionate is added. The reaction mixture is heated under reflux for 12 hours before filtering hot. The filtrate is evaporated under reduced pressure to give intermediate 1 a) as a yellow powder mp 76°.

b) a mixture of 12 g of polyethylene mono-alcohol ($M_n$ 460), 10 g (17.4 mol) of the compound from example 1a and 0.4 g of p-Toluensulphonic acid in 100 ml of mesitylene are heated at 140° C. and left to react for 8 hours.

The solution is washed twice with water and the organic layer is separated dried under sodium sulfate and evaporated under vacuum. A white powder is obtained with a melting range of 78-87° C.

$\epsilon$ at maximum $\lambda$ is 52400 lmol$^{-1}$ cm$^{-1}$.

Example A2

Synthesis of Compound 102 of Formula

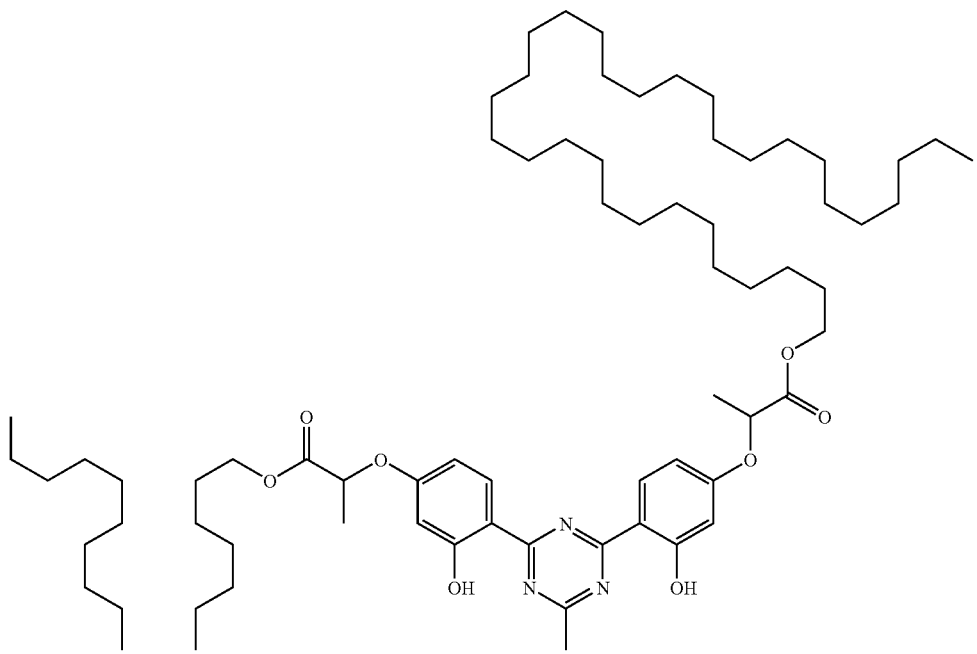

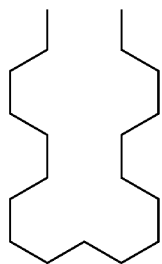
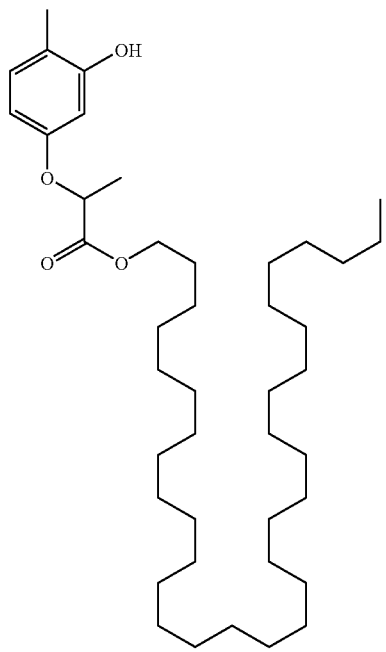

a) Synthesis of the Intermediate of Formula:

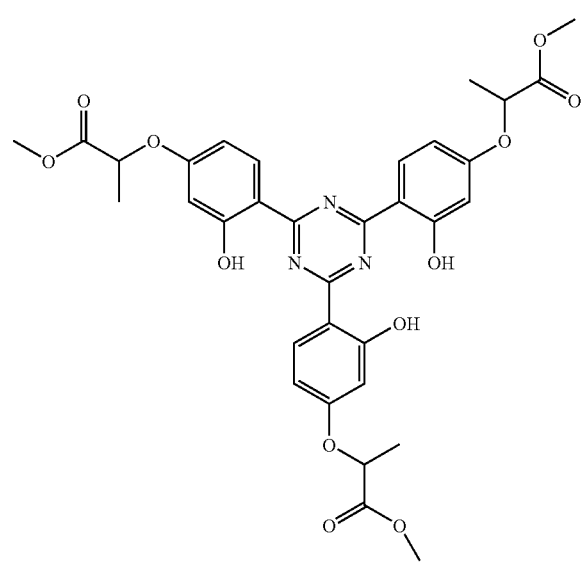

101 g 2,4,6-Tris-resorcinol-1,3,5-triazine and 87 g sodium carbonate are heated to 100° in 100 ml DMF. 181 g Methyl 2-bromopropionate in xylene is added dropwise over 1 hour and the reaction mixture stirred at 90° for a further 3 hours. The reaction mixture is then cooled to 30°, and filtered. The filtrate is evaporated under reduced pressure to give 166 g of an orange oil. This is dissolved in 400 ml isopropanol and 80 ml ethylmethylketone, cooled to 0° and filtered. After drying 125 g of the intermediate 2a) was isolated (mp 120°).

b) following the procedure described in the example 1-b, and using as starting material the compound of example 2-a; a pale yellow solid is obtained with melting range of 78-87° C.

$\epsilon$ at maximum $\lambda$ is 58400 lmol$^{-1}$ cm$^{-1}$.

Example A3

Synthesis of Compound 103 of Formula

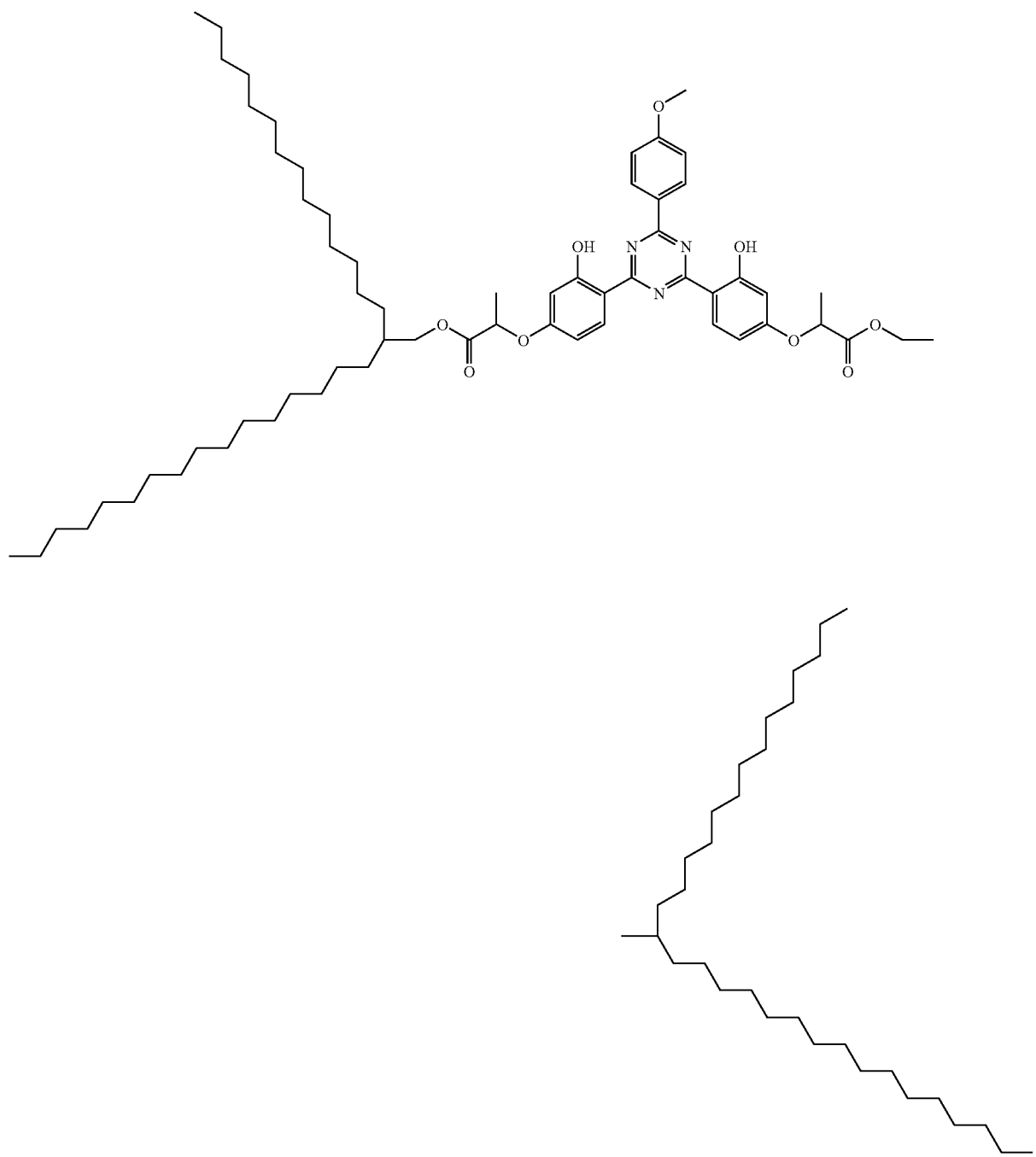

To a mixture of 2 g (0.0034 mol) of the intermediate of example 1-a and 4.24 g (0.0090 mol) of Isofol 32®, in 30 ml of mesitylene, 0.1 g of p-toluenesulphonic acid is added. The solution is heated at 165° C. and left to react for 4 hours (in this experimental conditions the solvent is eliminated and the reaction is essentially carried out in bulk). 20 ml of toluene is added the solution is washed twice with water, the organic layer is then separated, dried under sodium sulfate and evaporated. A waxy product is obtained.

$\epsilon$ at maximum $\lambda$ is 41400 lmol$^{-1}$ cm$^{-1}$.

Example A4
Synthesis of Compound 104 of Formula
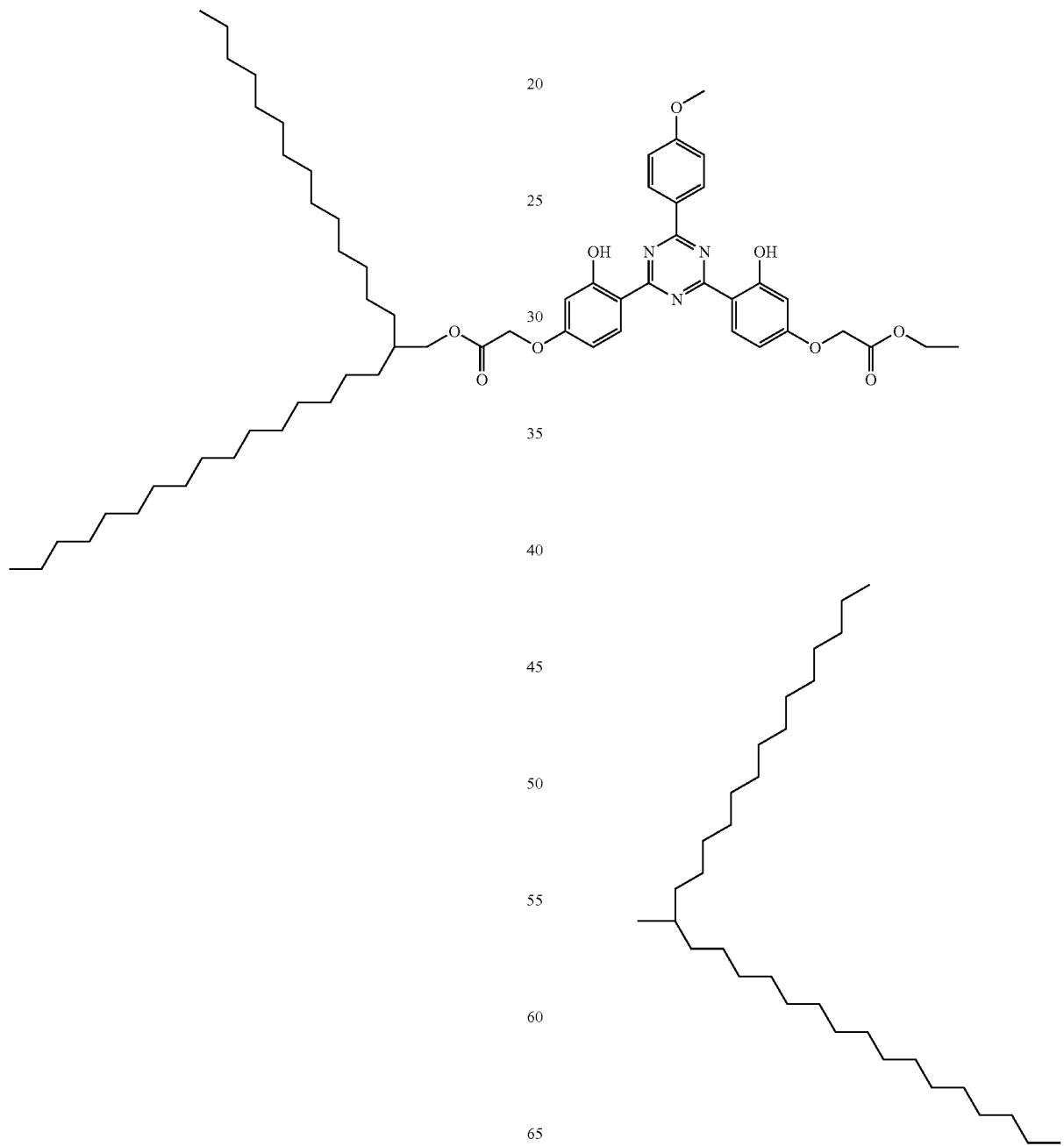

a) Synthesis of the Intermediate of Formula:

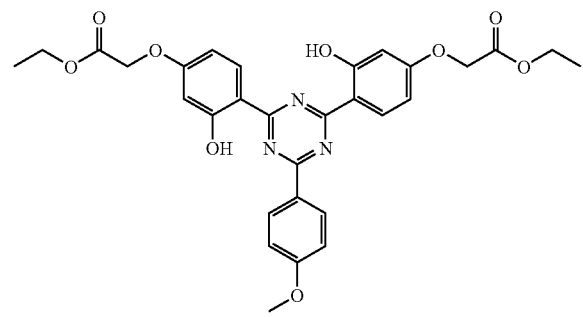

When the procedure used for intermediate 1a) is repeated but replacing methyl 2-bromopropionate with an equivalent amount of methyl bromoacetate, intermediate 3 a is isolated as a yellow powder (mp 216°).

b) following the procedure reported in example 3 and using the intermediate of example 4-a, a waxy product is obtained.

$\epsilon$ at maximum $\lambda$ is 42000 lmol$^{-1}$ cm$^{-1}$.

Example A5

Synthesis of Compound 105 of Formula

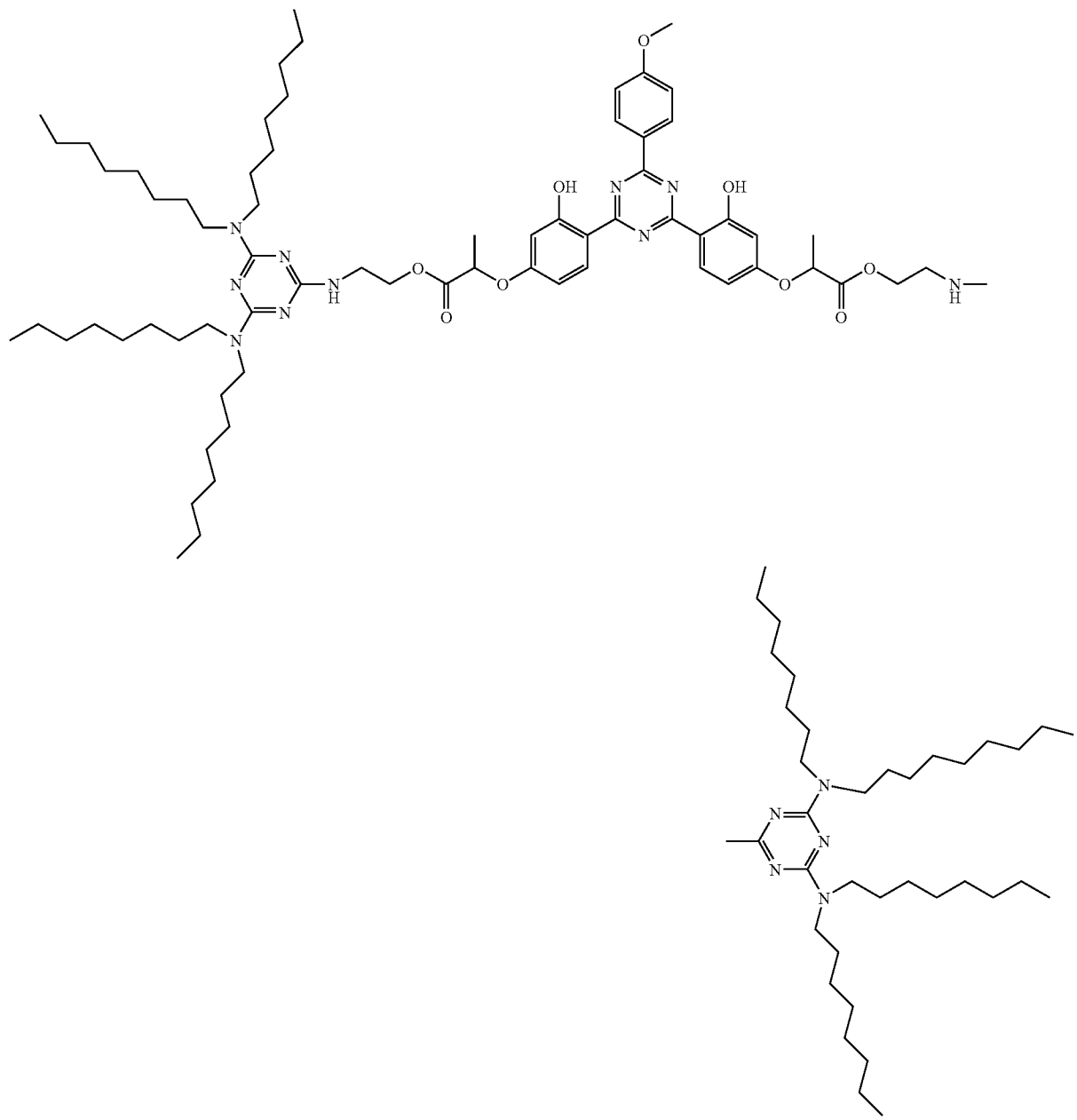

a) Synthesis of the Intermediate of Formula:

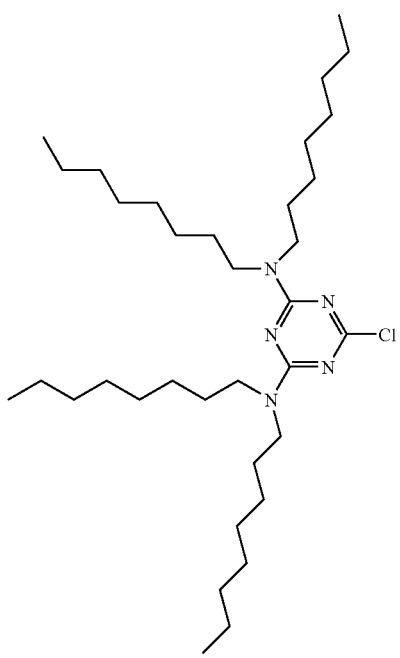

To a solution of 22.9 g (0.124 mol) of cyanuric chloride in 300 ml of toluene, 60 g (0.248 mol) of dioctylamine are slowly added. After the addition, the mixture is left to react for half an hour and then 10.8 g (0.27 mol) of NaOH in 20 ml of water are added. The mixture is heated at 90° C. and left to react for additional 1 hour. The water is azeotropically removed. The organic layer is then dried under sodium sulfate, filtered and concentrated under vacuum. A yellow oil is obtained.

b) Synthesis of the Intermediate of Formula:

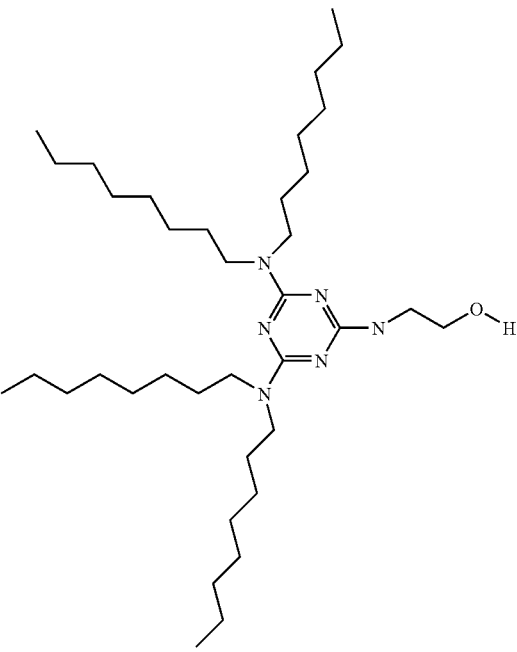

A solution of 60 g (0.1 mol) of the intermediate of example 5-a and 200 ml of ethanolamine in 150 ml of mesitylene is heated at 150° C. for 1 hour. The upper phase is recovered and washed twice with a slightly acidic water solution (HCl). It is then dried under sodium sulfate, filtered and evaporated. A white solid is obtained.

c) a mixture of 48.3 g (0.078 mol) of the compound of example 5-5 and 22.45 g (0.039 mol) of the compound of example 1-b in 40 ml of mesitylene are heated at 165° C. in presence of 1.0 g of dibutyltinozide. The mixture is left to react for 4 hours. (in this experimental conditions the solvent is eliminated and the reaction is essentially carried out in bulk). At room temperature 400 ml of toluene and 40 g of silica are added. After 1 hour the solution is filtered off and evaporated under vacuum. A product is obtained with melting point of 63° C.

$\epsilon$ at maximum $\lambda$ is 78700 mol$^{-1}$ cm$^{-1}$.

Example A6
Synthesis of Compound Formula
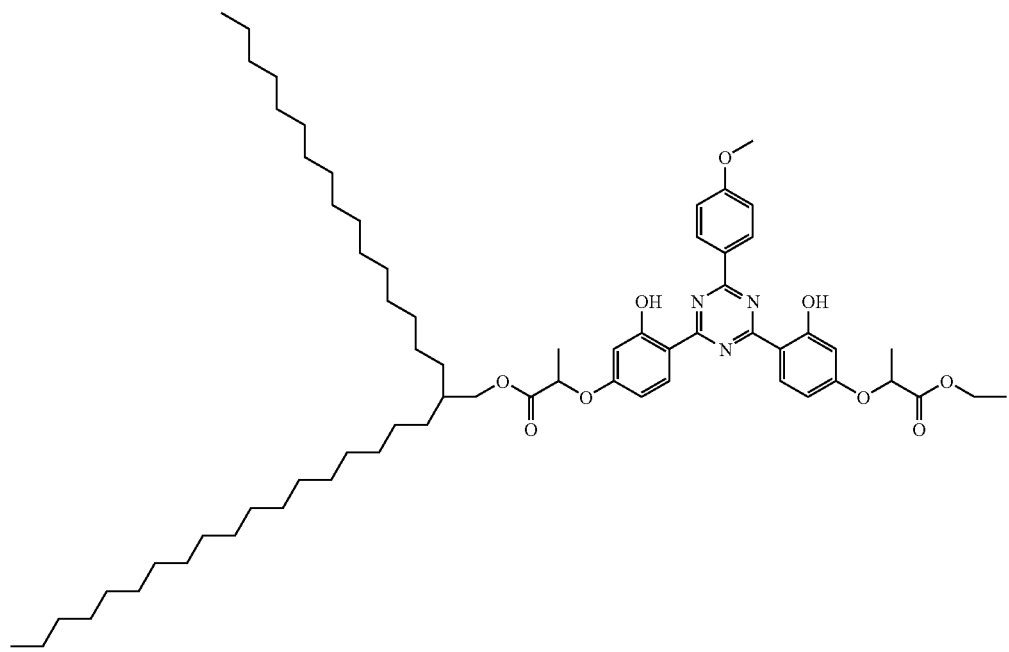
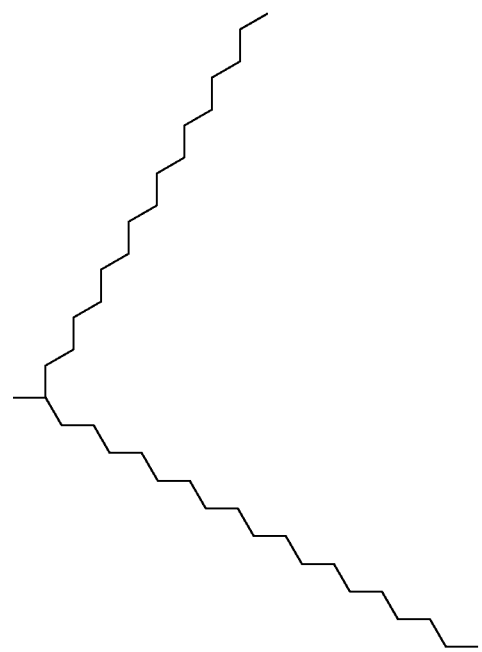

Following the procedure described in the example 1 and using as starting material the compound if example 1-a Isofol 36®, a waxy product has been obtained.

$\epsilon$ at maximum $\lambda$ is 38900 $lmol^{-1}$ $cm^{-1}$.

Example A7

Synthesis of Compound 107 of Formula

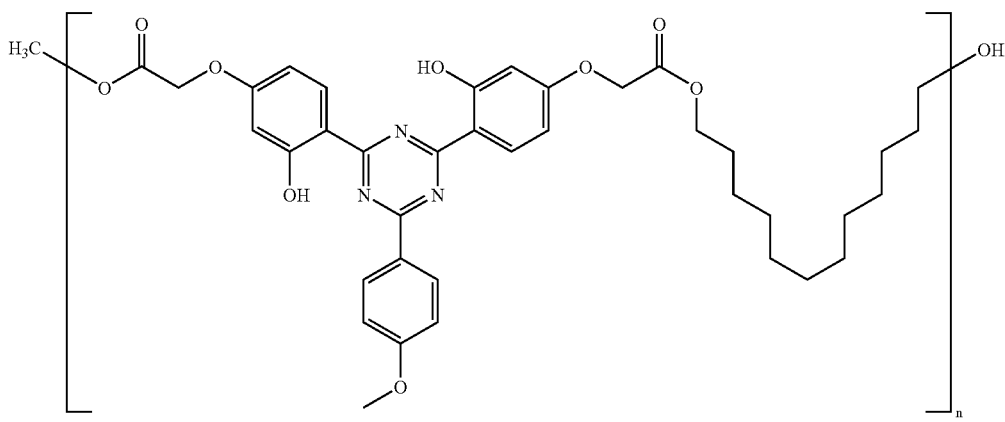

a) Synthesis of the Intermediate of Formula

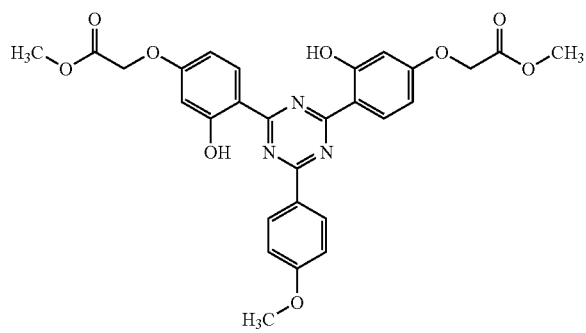

To a suspension of 100 g of 2-(4-methoxyphenyl)-4,6-bis-resorcinol-1,3,5-triazine (0.248 moles) in 400 ml of methanol at room temperature, 102 ml of $CH_3ONa$ (30% W/W in $CH_3OH$; 0.54 moles) are added.

The solution is then heated up to 50° C., and 101 g (0.66 moles) of methyl 2-bromoacetate is added dropwise over 1 hour.

The mixture is heated under reflux for 2 hours and 200 ml of methanol are distilled off; 400 ml of xylene and 51 g (0.37 moles) of potassium carbonate are added to the mixture and the suspension is heated to 120° C. for 6 hours. The mixture is cooled to 80° C. and washed twice with 100 ml of water. The organic layer is then dried under vacuum.

b) A mixture of 20 g (0.036 mol) of the compound from the above part (a) and 8.1 g (0.040 mol) of 1,12-dodecanediole in 100 ml of 1,2-dichlorobenzene are heated up to 180° C. in presence of 1 g of p-toluenesulfonic acid. After 30 hours the reaction mixture is washed twice with water, dried under sodium sulphate and evaporated under reduced pressure. A pale brown solid is obtained, melting range 94-105° C.;

$\epsilon$ at $\lambda_{max}$ is 41200 $l\ mol^{-1}$ $cm^{-1}$. Mn=2000; PDI=1.73.

Example A8
Synthesis of Compound 108 Formula
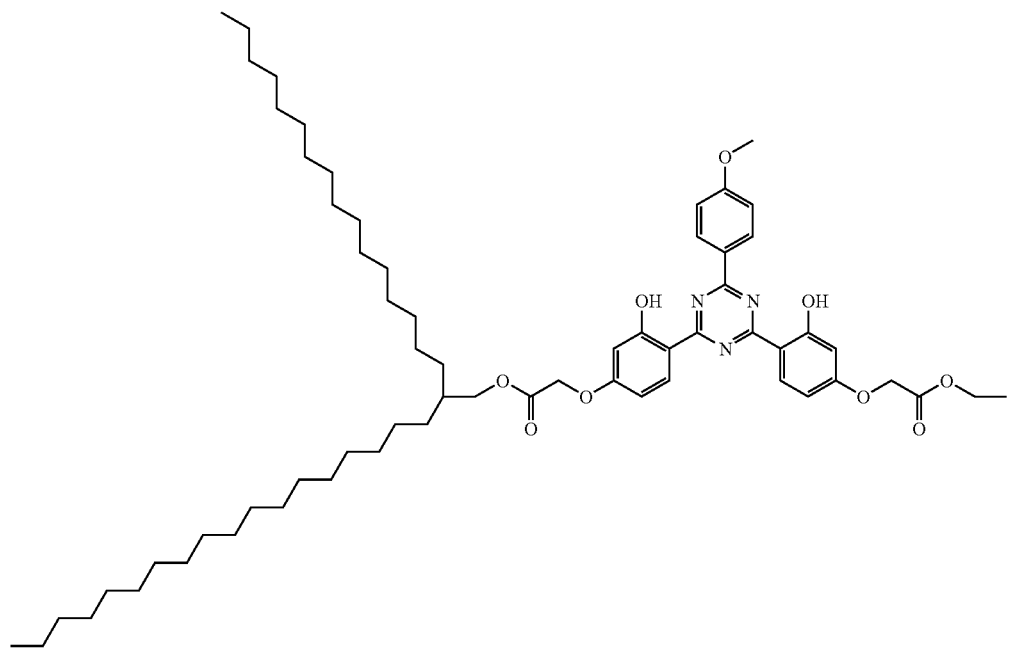
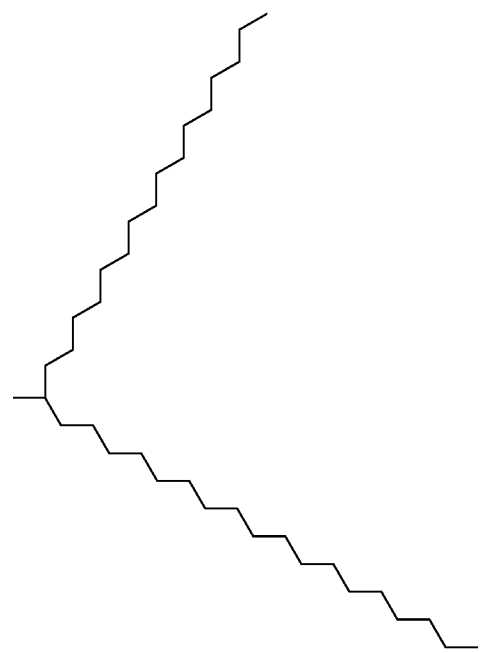

Following the procedure described in the example 1, the reported compound has been obtained as a yellow solid.

Melting range of 36-43° C. $\epsilon$ at maximum $\lambda$ is 58400 lmol$^{-1}$ cm$^{-1}$.

Example A9

Synthesis of Compound 109 of Formula

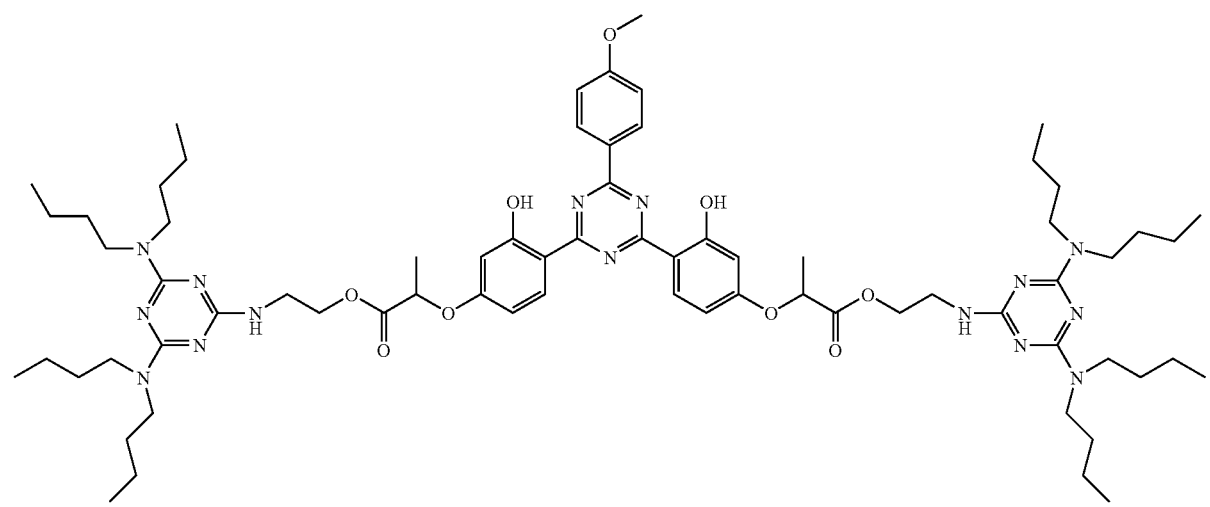

Following the procedure described in the example 5 the reported molecule has been obtained as a white solid.

Melting range is 46-54° C. and $\epsilon$ at maximum $\lambda$ is 83000 lmol$^{-1}$ cm$^{-1}$.

Example A10

Synthesis of the compound 110 of formula:

A mixture of 20 g (0.0347 mol) of compound from example A1 part a, 14.1 g (0.096 mol) of dodecanediol, 8 g (0.0347 mol) of dimethylsebacate and 0.5 g of p-toluenesulfonic acid (pTSA) in 20 ml of mesitylene is heated up to 160° C., the distilled mesitylene is discarded. After about 6 hours the mixture is cooled and 200 ml of toluene are added. The organic layer is washed twice with 100 ml of a water solution of sodium carbonate, dried under sodium sulphate and evaporated under reduced pressure. A yellow-orange resin is obtained.

$\epsilon$ at maximum $\lambda$ is 45199 lmol$^{-1}$ cm$^{-1}$; Mn=5700 g/mol; PDI=2.6.

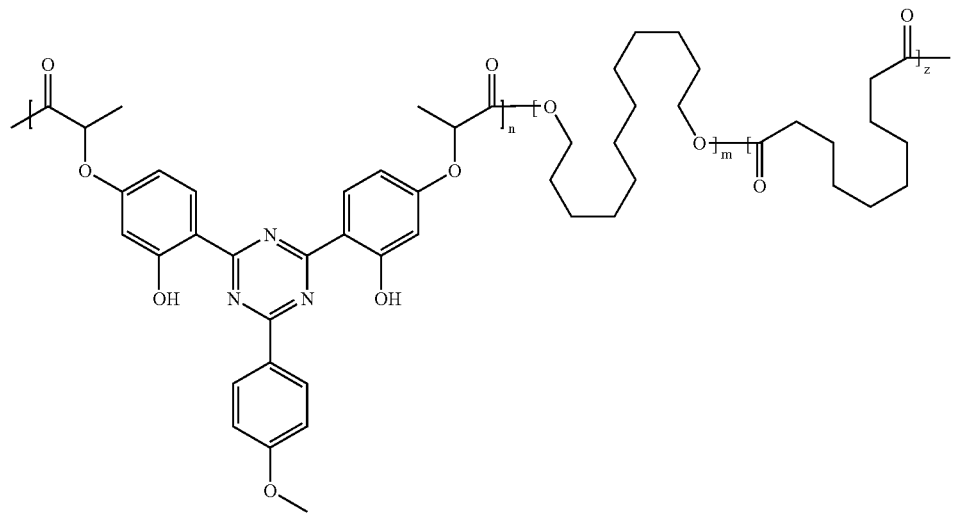

with monomer ratio n:m:z=0.5:1:0.5.

Example A12

Synthesis of the Compound 112 of Formula

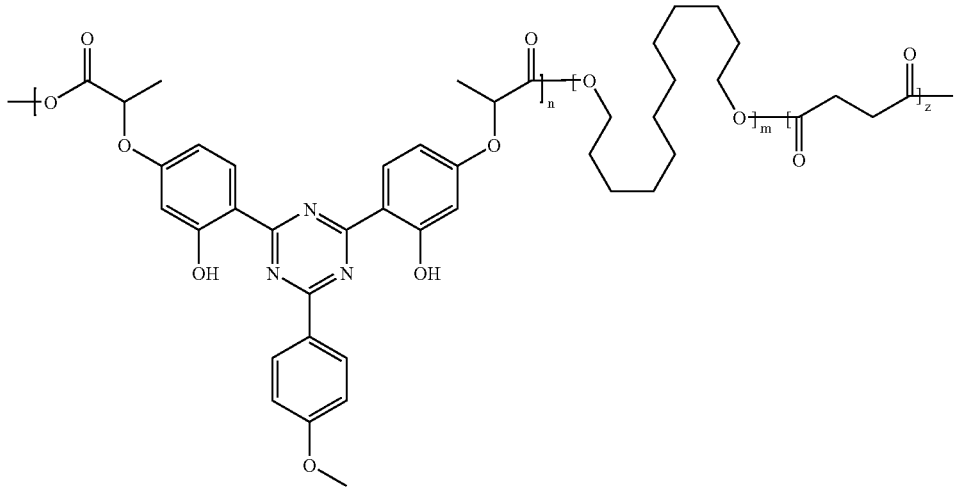

with monomer ratio n:m:z=0.5:1:0.5.

A mixture of 25 g (0.043 mol) of compound from example A1 part a, 20.9 g (0.103 mol) of dodecanediol, 6.2 g (0.043 mol) of dimethylsuccinate and 0.5 g of p-toluenesulfonic acid (pTSA) in 30 ml of mesitylene is heated up to 160° C. and the distilled mesitylene is discarded. After about 6 hours the mixture is cooled and 200 ml of toluene are added. The organic layer is washed twice with 100 ml of a water solution of sodium carbonate, dried under sodium sulphate and evaporated under reduced pressure.

A yellow-orange resin is obtained.

$\epsilon$ at maximum $\lambda$ is 47335 lmol$^{-1}$ cm$^{-1}$; Mn=3400; PDI=1.9.

Example A13

Synthesis of the Compound 113 of Formula with monomer ratio n:m:z:=0.5:1:0.5.

A mixture of 59.8 g (0.15 mol) of compound from example A1 part a, 41.6 g (0.206 mol) of dodecanediol, 28.4 g (0.103 mol) of dimethyl-L-tartrate and 1 g of p-toluenesulfonic acid (pTSA) in 200 ml of mesitylene is heated up to 160° C. and the distilled mesitylene is discarded. After about 6 hours the mixture is cooled and 200 ml of toluene are added. The organic layer is washed twice with 200 ml of a water solution of sodium carbonate, dried under sodium sulphate and evaporated under reduced pressure. A yellow powder is obtained. M.p.: 75-105° C.; $\epsilon$ at maximum $\lambda$ is 38670 l mol$^{-1}$ cm$^{-1}$; Mn=3400; PDI=2.4.

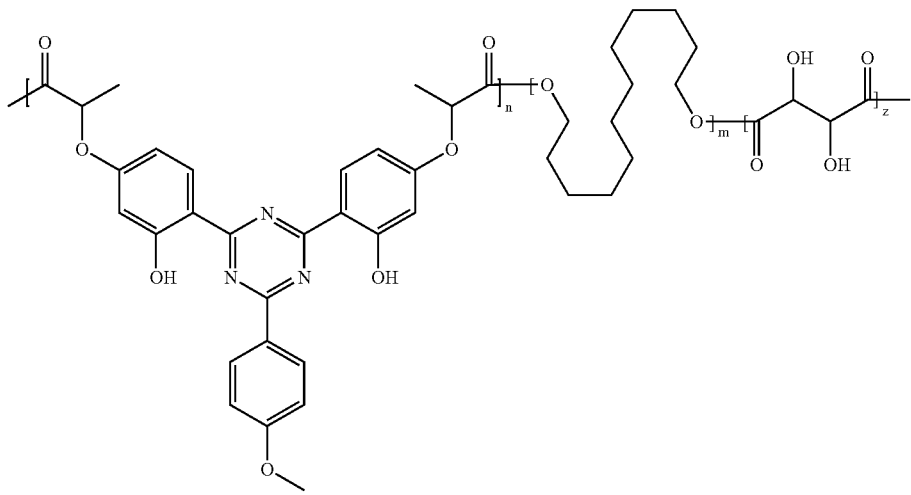

Example A 14

Synthesis of the Compound 114 of Formula:

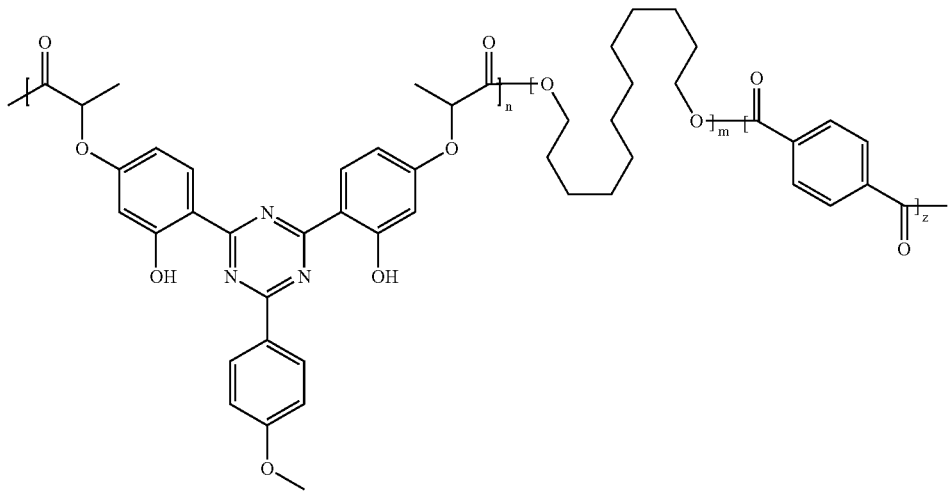

with monomer ratio n:m:z:=0.5:1:0.5.

Following the experimental conditions described in the example A13 and using dimethylterephthalate instead of dimethyltartrate, the polymer having the structure and the composition reported above is obtained as a yellow powder. Melting range 65-75° C.

$\epsilon$ at maximum $\lambda$ is 45210 lmol$^{-1}$ cm$^{-1}$; Mn=6000; PDI=1.8.

Example A 15

Synthesis of the Compound 115 of Formula:

Following the experimental conditions described in the example A10 and using as starting material the compound from example A7 part a, the polymer having the structure and the composition reported above is obtained as a yellow-orange resin.

$\epsilon$ at maximum $\lambda$ is 41030 l mol$^{-1}$ cm$^{-1}$; Mn=5900; PDI=2.3.

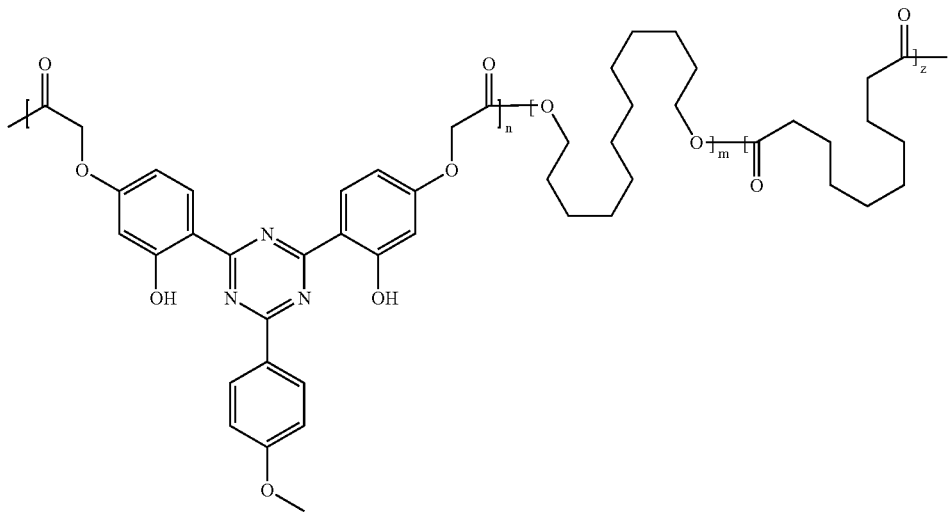

n = 0.5; m = 1; z = 0.5 with monomer ratio n:m:z:=0.5:1:0.5.

Example A 16

Synthesis of the compound 116 of Structure:

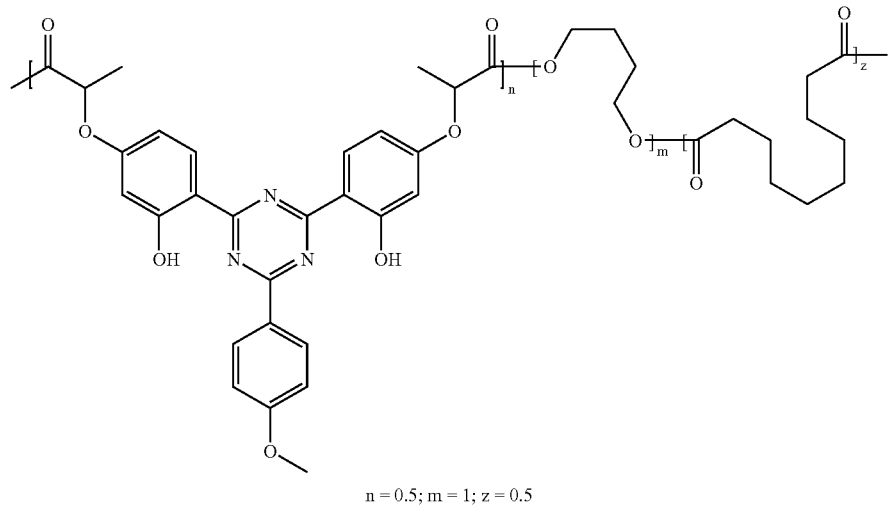

n = 0.5; m = 1; z = 0.5 with monomer ratio n:m:z:=0.5:1:0.5.

Following the experimental procedure described in the example A12 and using butanediole instead of dodecanediole, the polymer having the structure and the composition reported above is obtained as a yellow-orange powder. Melting range 55-65° C.

$\epsilon$ at maximum $\lambda$ is 37071 l mol$^{-1}$ cm$^{-1}$; Mn=2100; PDI=1.8.

Example A 17

Synthesis of the compound 117 of formula:

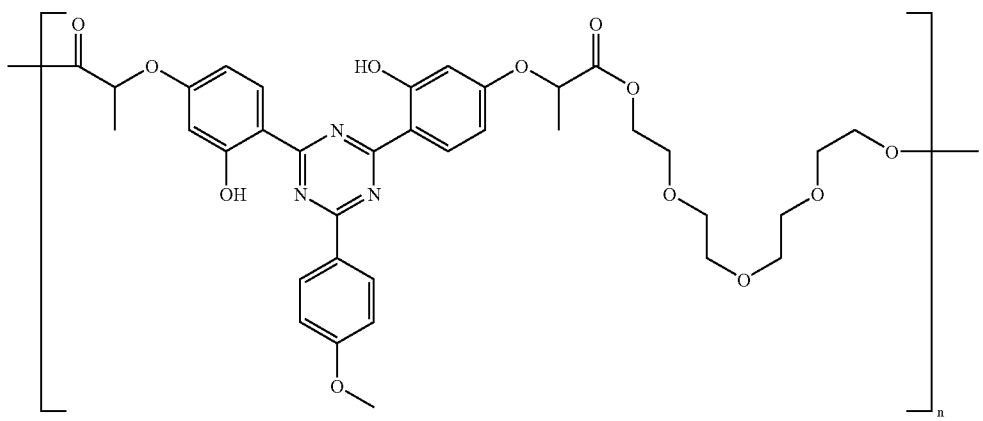

Following the synthetic procedure reported in the example A7-b, and using as starting material the intermediate from example A1, part a and PEG 200 (polyethylene glycol with 200 as molecular weight), the above polymer is obtained. Melting Range 90-97° C.

$\epsilon$ at max $\lambda$ is 37071 l mol$^{-1}$ cm$^{-1}$. Mn=4300; PDI=1.8.

Example A18

Synthesis of the Compound 118 of Formula:

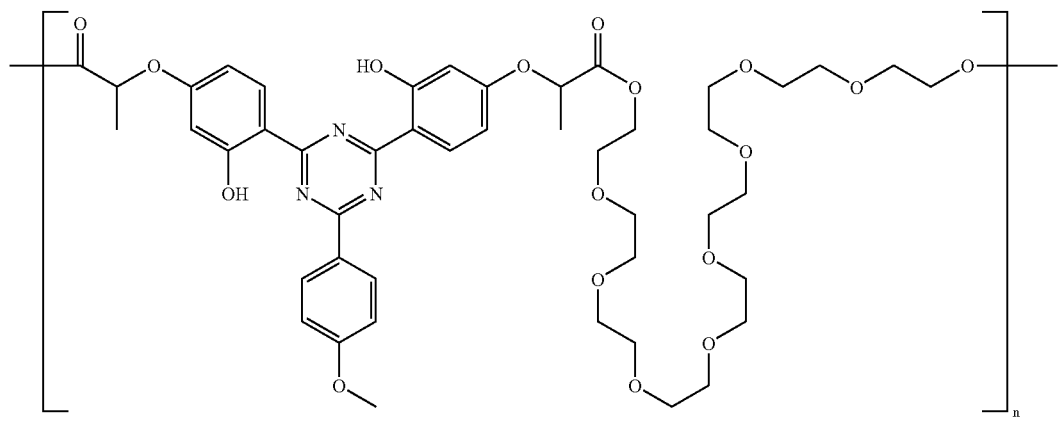

Following the synthetic procedure reported in the example A7-b, and using as starting material the intermediate from example A1, part a and PEG 400 (poly ethylene glycol with 400 as molecular weight), the polymer in the structure above is obtained as a waxy product.

ε at max λ is 46911 l mol$^{-1}$ cm$^{-1}$. Mn=4300; PDI=1.8.

Example A 19

Synthesis of the Compound 119 of Formula:

Following the synthetic procedure reported in the example A7-b, and using as starting material the intermediate from example A1, part a and PEG 600 (poly ethylene glycol with 600 as molecular weight), the polymer in the structure above is obtained as a waxy product.

ε at max λ is 42473 l mol$^{-1}$ cm$^{-1}$. Mn=5600; PDI=3.

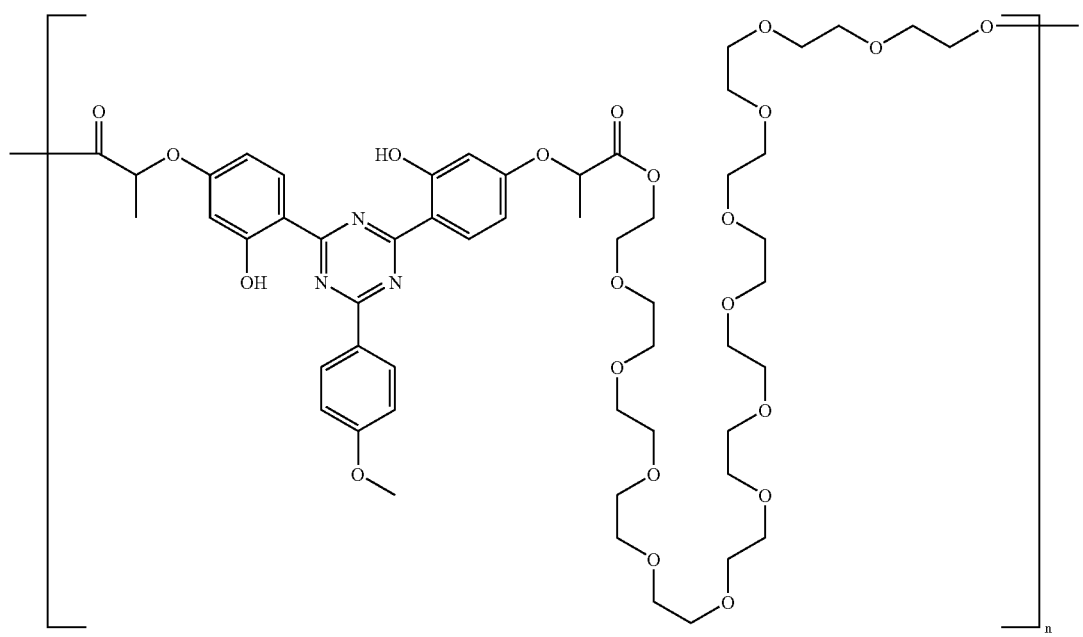

Example A20

Synthesis of the Compound 120 of Formula:

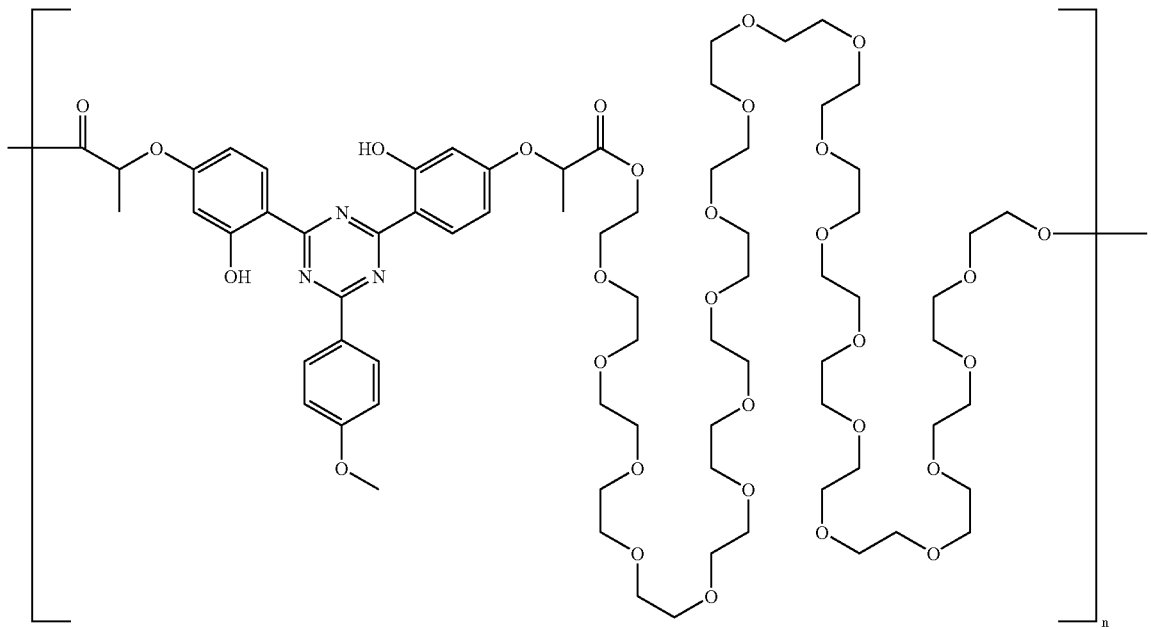

Following the synthetic procedure reported in the example A7-b, and using as starting material the intermediate from example A1, part a and PEG 1000 (poly ethylene glycol with 1000 as molecular weight), the polymer in the structure above is obtained as a waxy product.

ε at max λ is 54315 l mol$^{-1}$ cm$^{-1}$. Mn=7000; PDI=1.6.

Example A 21

Synthesis of the Compound 121 of Formula:

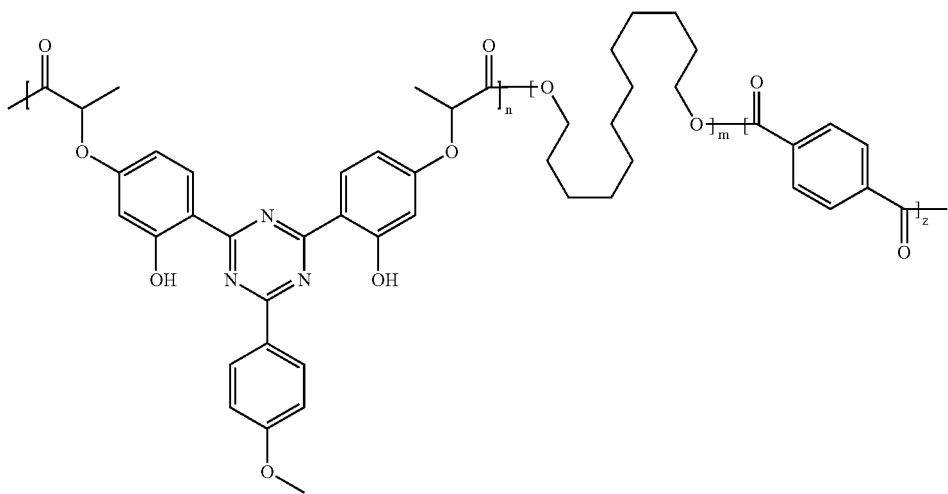

with monomer ratio n:m:z:=1:1.5:0.5.

Following the experimental condition described in the example A13, the polymer having the structure and the composition reported above is obtained as a yellow powder. Melting range: 85-95° C. ε at max λ is 52414 l mol$^{-1}$ cm$^{-1}$.

Example A22

Synthesis of the compound 122 of formula:

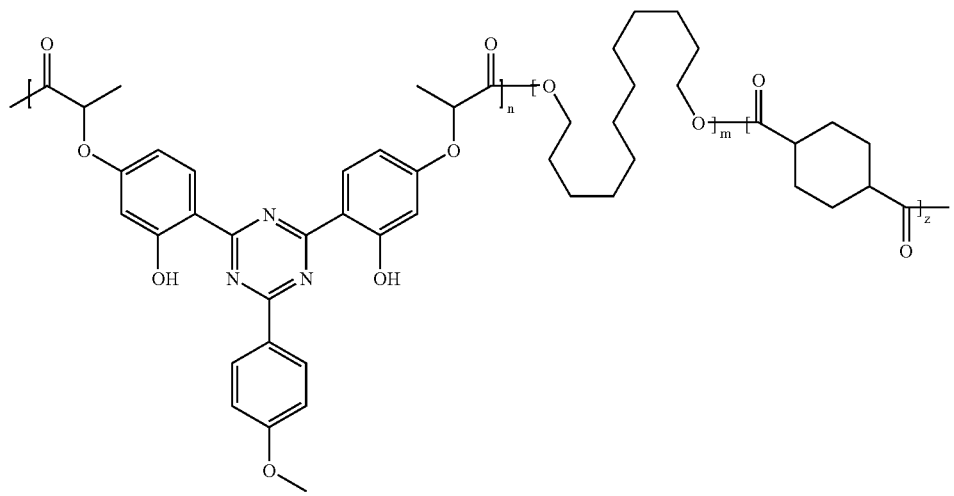

with monomer ratio n:m:z:=1:1.5:0.5.

Following the experimental condition described in the example A13, the polymer having the structure and the composition reported in the structure above is obtained as a yellow powder. ε at max λ is 53891 l mol$^{-1}$ cm$^{-1}$. Mn=6200; PDI=2.

Example A 23

Synthesis of the Compound 123 of Formula:

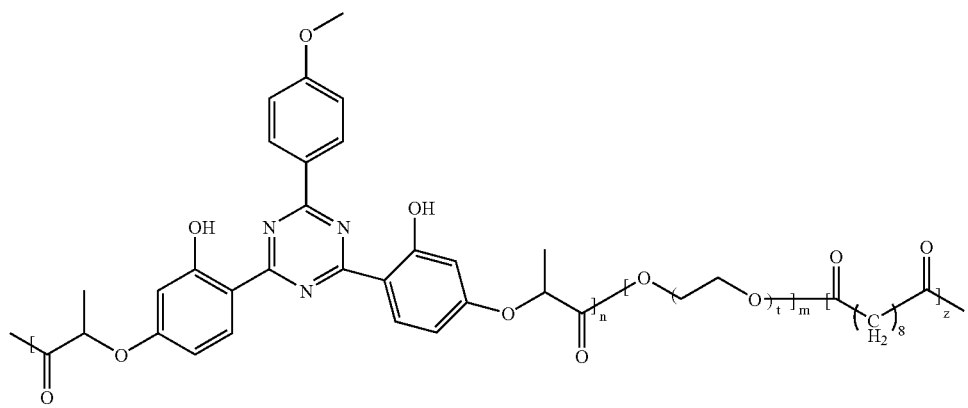

with monomer ratio n:m:z:=1:1.5:0.5.

Following the synthetic procedure reported in the example A13, and using as starting material the intermediate from example A1, part a and PEG 200 (poly ethylene glycol with 200 as molecular weight), the polymer having the structure and the composition reported above is obtained. $\epsilon$ at max $\lambda$: 42733. Mn=4600. PDI=2.1.

Example A 24

Synthesis of the Compound 124 of Formula:

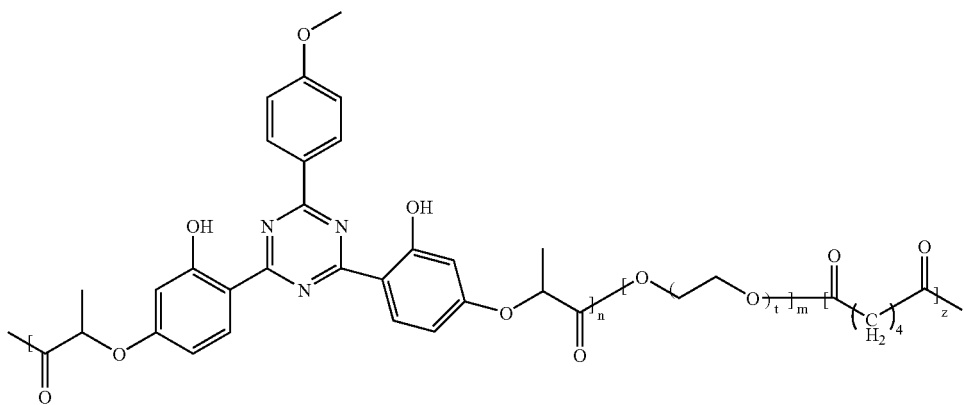

with monomer ratio n:m:z:=1:1.5:0.5.

Following the synthetic procedure reported in the example A13, and using as starting material the intermediate from example A1, part a and PEG 200 (poly ethylene glycol with 200 as molecular weight), the polymer having the structure and the composition reported above is obtained. $\epsilon$ at max $\lambda$: 41305; Mn=5300; PDI=2.3.

Example A 25

Synthesis of the Compound 125 of Formula:

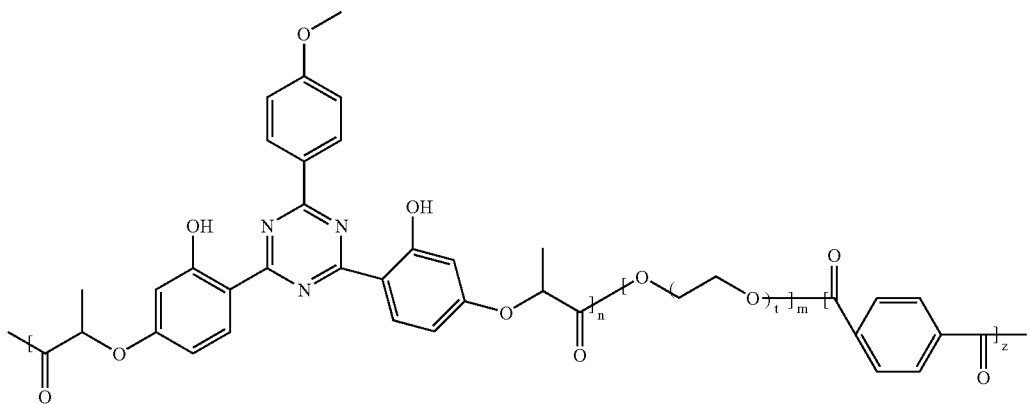

with monomer ratio n:m:z:=1:1.5:0.5.

Following the synthetic procedure reported in the example A13, and using as starting material the intermediate from example A1, part a and PEG 200 (poly ethylene glycol with 200 as molecular weight), the polymer having the structure and the composition reported above is obtained. $\epsilon$ at max $\lambda$: 44735; Mn=4500; PDI=2.1.

Example A 26

Synthesis of the Compound 126 of Formula:

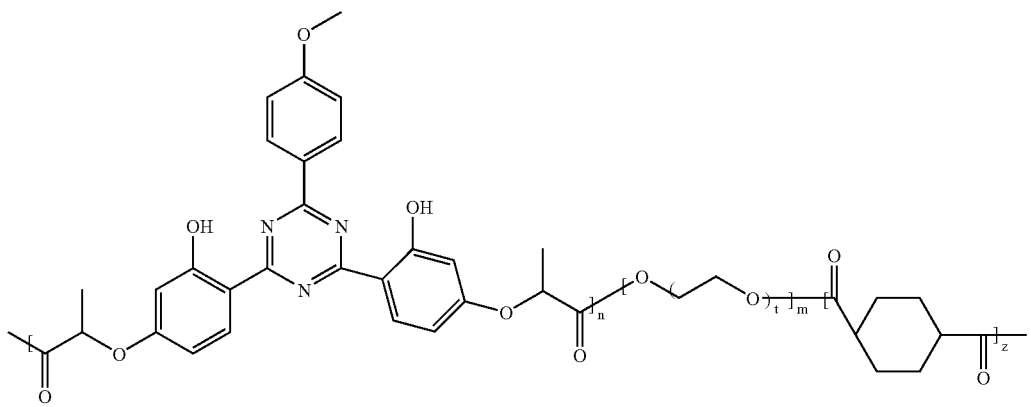

with monomer ratio n:m:z:=1:1.5:0.5.

Following the synthetic procedure reported in the example A13, and using as starting material the intermediate from example A1, part a and PEG 200 (poly ethylene glycol with 200 as molecular weight), the polymer having the structure and the composition reported above is obtained. $\epsilon$ at max $\lambda$: 48534; Mn=3700; PDI=1.7.

Example A 27

Synthesis of the Compound 127 of Formula:

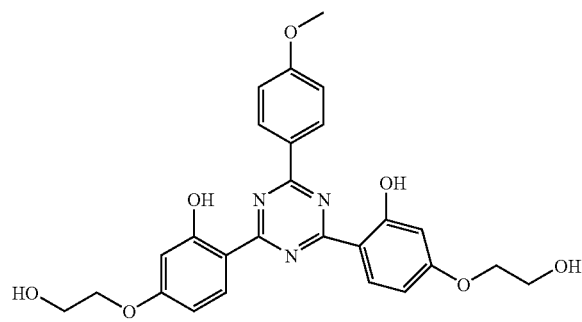

A suspension of 20 g (0.05 mole) of 2-(4-methoxyphenyl)-4,6-bis(2,4-dihydroxyphenyl)-1,3,5-triazine in 100 ml ethylcellosolve is heated to 70° C. 44 g potassium carbonate are added and 40.16 g (0.32 mole) 2-bromoethanol are added dropwise over 2 hrs. The mixture is heated for a further 3 hours at 70° C., then filtered hot to remove inorganic salts. The filtrate is cooled to 0° C. and allowed to crystallise. The solid is filtered off and dried at 60° C. under vacuum, yielding 11.1 g of 2-(4-methoxylphenyl)-4,6-bis(2-hydroxy-4-(2-ethoxyethoxy)phenyl)-1,3,5-triazine as a yellow powder, m.p. 155-158° C.

Example A 28

Synthesis of the Compound 128 of Formula:

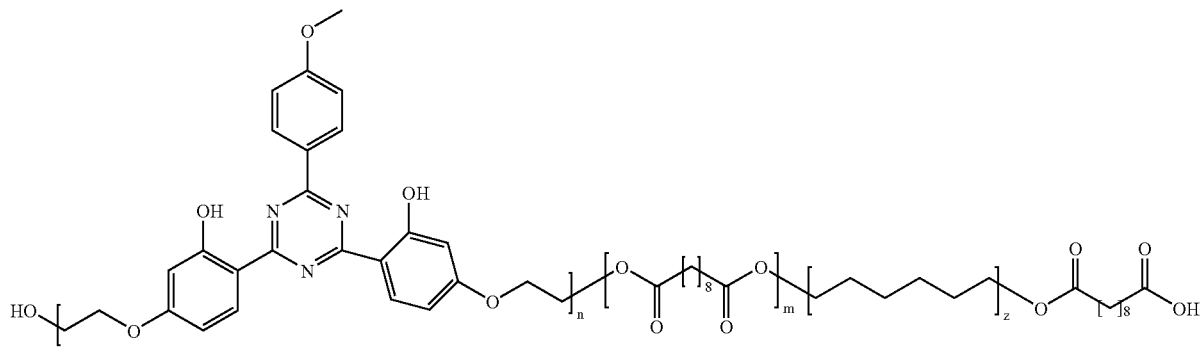

with monomer ratio n:m:z:=1:1.5:0.5.

The mixture of 49.15 g (0.1 mol) of compound from example A 27, 5.9 g (0.05 mol) of 1,6-hexanediol, 30.3 g (0.15 mol) of sebacic acid and 1 g of p-toluenesulfonic acid in 200 ml of mesitylene is heated up to 160° C. and the distilled mesitylene is discarded. After about 6 hours the mixture is cooled and 200 ml of toluene are added. The organic layer is washed twice with 200 ml of water solution of sodium carbonate, dried under sodium sulfate and evaporated under reduced pressure.

Example A 29

Synthesis of the Compound 129 of Formula:

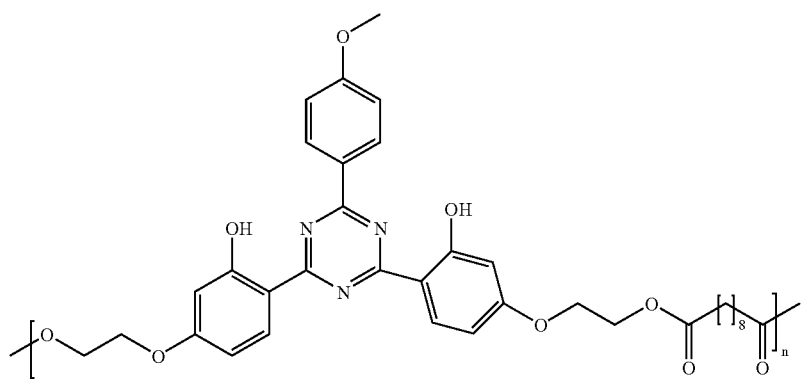

The mixture of 44.7 g (0.091 mol) of the compound from example A 27, 20.9 g (0.091 mol) of dimethylsebacate and 1 g of p-toluenesulphonic acid in 60 ml of xylene is heated up to 160° C. and the distilled mesitylene is discarded. After about 6 hours the mixture is cooled and 200 ml of toluene are added. The organic layer is washed twice with 200 ml of water solution of sodium carbonate, dried under sodium sulfate and evaporated under reduced pressure.

B: Application Examples

Example B1

A formulation containing 2% by weight of compound 101 is prepared, according to the following procedure: the compound is mixed with milled LLDPE (Dowlex® NG 5056E, Dow Chemical), characterized by a density of 0.919 g/cm$^3$ and a melt flow index (190° C./2.16 Kg) of 1.1) and extruded at a maximum temperature of 230° C. in a OMC twin-screw extruder. The granules so obtained are blown in a lab-scale Formac blow-extruder at a maximum temperature of 230° C. to give a film of about 50 μm thickness.

A UV-Vis spectrum of the film is recorded in the range 200-800 nm by means of a Perkin-Elmer lambda 20 spectrophotometer, equipped with a RSA-PE-20 Labsphere integrating sphere. The spectrum so obtained displays a strong absorption in the UV range with a maximum at about 310 nm and a shoulder around 345 nm, while the absorption is negligible in the visible part of the spectrum; the transmittance is 13% in the range 280-400 nm and of 7% in the range 280-390 nm. Transmittance value is 31% at 380 nm.

A piece of the film is stored at room temperature inside an envelope and between two pieces of paper. The film is periodically inspected visually to verify possible exudation (blooming) of the compound from the bulk of the polymeric matrix. After 1500 hours no visual blooming occurrs. Another piece of the film is placed in a forced circulating air oven at 60° C. for the same reason. Again, after 1500 hours no visual blooming occurrs. Another piece of the same film is placed under fluorescent bulbs of the same type used in supermarkets and dairy cases. UV-Vis spectra of the film are periodically taken to verify modifications of the absorption due to photochemical degradation of the compound. After 1500 hours of exposure, the spectrum still displays 85% of the initial absorption at 345 nm.

Example B2

A formulation containing 2% by weight of compound 102 was prepared, according to the procedure described in Example 1.

The 50 μm thick film so obtained was subjected to UV-Vis spectrophotometry, as described in Example 1. The film displays a strong absorption in the UV range with a maximum at 359 nm, while the absorption is negligible in the visible part of the spectrum; the transmittance is of 9% in the range 280-400 nm and of 5% in the range 280-390 nm. Transmittance value is 6% at 380 nm.

Pieces of the same film were stored at room temperature and at 60° C. respectively, as described in Example 1. After 1500 hours no visual blooming occurred in both cases. Another piece of film is exposed under fluorescent bulbs as in Example 1. After 1500 hours 95% of the initial absorption at 359 nm are retained.

Example B3

A formulation containing 1.5% by weight of compound 107 was prepared, according to the procedure described in Example 1.

The 50 μm thick film so obtained was subjected to UV-Vis spectrophotometry, as described in Example 1. The film displays a strong absorption in the UV range with a maximum at 345 nm, while the absorption is negligible in the visible part of the spectrum; the transmittance is of 11% in the range 280-400 nm and of 7% in the range 280-390 nm. Transmittance value is 15% at 380 nm.

Pieces of the same film were stored at room temperature and at 60° C. respectively, as Example 1. After 1500 hours no visual blooming occurred in both cases. Another piece of film is exposed under fluorescent bulbs as in Example 1. After 1500 hours 100% of the initial absorption at 345 nm are retained.

Example B4

The following formulations are prepared according to the procedure described in example B1:

| Compound | % by weight in LLDPE film |
|---|---|
| 110 | 1.5 |
| 113 | 2 |
| 114 | 2 |
| 117 | 1.5 |
| 120 | 2.5 |
| 121 | 1.5 |

The 50 μm thick film so obtained are subjected to UV-Vis spectrophotometry, as described in Example B1. The films display a strong absorption in the UV range, while the absorption is negligible in the visible part of the spectrum. The main characteristics are summarized in the following table.

| Compound | Absorption maximum (nm) in the region 330-360 nm | % Transmittance 280-400 nm | % Transmittance 280-390 nm | % Transmittance at 380 nm |
|---|---|---|---|---|
| 110 | 339 | 8 | 14 | 26 |
| 113 | 340 | 14 | 20 | 25 |
| 114 | 343 | 8 | 13 | 17 |
| 117 | 345 | 8 | 12 | 16 |
| 120 | 342 | 11 | 16 | 25 |
| 121 | 346 | 8 | 12 | 13 |

In terms of visual blooming, the films containing the above compounds behave as those described examples B1, B2 and B3, both at room temperature and at 60° C. in a forced circulating air oven.

The films are investigated further as regards the compatibility of the additives therein, in terms of resistance to extraction by lipophilic liquids. To do so, pieces of the films described in this example are dipped into olive oil inside a covered Petri dish and exposed to heat at 60° C. in an oven for 10 days. At the end of this period the films are taken away from the oil, rinsed with n-hexane to remove the oil in excess which could not drip spontaneously from the film, dried and finally subjected to UV spectroscopy, measuring the retained absorption at maximum of the additive. The results are reported in the following table.

| Compound | % retained absorption at maximum |
|---|---|
| 110 | 95 |
| 113 | 93 |
| 114 | 97 |
| 117 | 97 |

-continued

| Compound | % retained absorption at maximum |
|---|---|
| 120 | 95 |
| 121 | 98 |

The UV absorbers of the invention show good persistence in the film.

The invention claimed is:

1. An hydroxyphenyltriazine compound of formula (I) or (Ib)

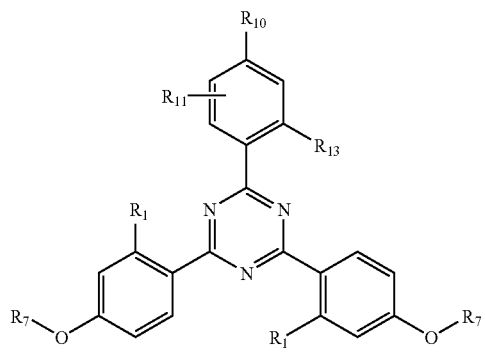

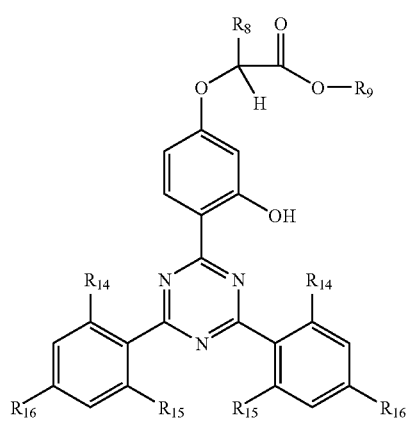

in which
R$_1$ are independently of each other H or OR$_7$, with the proviso that at least one of R$_1$ or R$_{13}$ is OH;
R$_7$ are independently of each other hydrogen, C$_1$-C$_{12}$alkyl or a radical of formula (III),

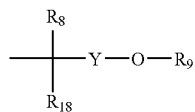

wherein in formula (I) at least one R$_7$ is a radical of formula (III);

R$_8$ is hydrogen, C$_1$-C$_{18}$alkyl, C$_5$-C$_{12}$cycloalkyl, C$_2$-C$_{18}$alkenyl, phenyl, C$_7$-C$_{11}$phenylalkyl, C$_7$-C$_{11}$alkylphenyl, C$_1$-C$_{18}$alkyl substituted by phenyl, OH or halogen; C$_1$-C$_{18}$alkoxy, C$_5$-C$_{12}$cycloalkoxy, C$_3$-C$_{18}$alkenyloxy or COOH;

Y is —CO— or C$_1$-C$_{12}$alkylene;

R$_9$ in formula (III), if Y is —CO—, and R$_9$ in formula (Ib) are C$_{20}$-C$_{60}$ alkyl, C$_{20}$-C$_{60}$alkyl substituted by OH and/or interrupted by O, or is C$_{20}$-C$_{60}$alkenyl, or is a group of formula (IV),

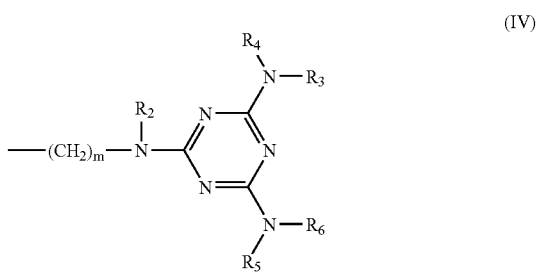

wherein m is a number from 1 to 20;

R$_9$ in formula (III), if Y is alkylene, is C$_{20}$-C$_{60}$alkanoyl;

R$_2$, R$_3$, R$_4$, R$_5$ and R$_6$ are independently of each other hydrogen, C$_1$-C$_{38}$alkyl which is unsubstituted or substituted by hydroxy or C$_1$-C$_8$alkoxy; or C$_1$-C$_{38}$alkyl which is interrupted by an oxygen atom or a N(C$_1$-C$_{18}$)alkyl group; or phenyl or C$_7$-C$_{12}$phenylalkyl which are unsubstituted or substituted by hydroxy or C$_1$-C$_8$alkyl;

R$_{10}$ is hydrogen, C$_1$-C$_4$alkyl, Cl, phenyl or a group —OR$_7$;

R$_{11}$ is hydrogen or methyl;

R$_{13}$ is hydrogen, methyl, OH or OR$_7$;

R$_{14}$ and R$_{15}$ are independently hydrogen, C$_1$-C$_8$alkyl, Cl or a group OR$_7$;

R$_{16}$ is is hydrogen, C$_1$-C$_8$alkyl, Cl or phenyl; and

R$_{18}$ is hydrogen or C$_1$-C$_8$alkyl.

2. A compound according to claim 1 of formula (I) or (Ib)

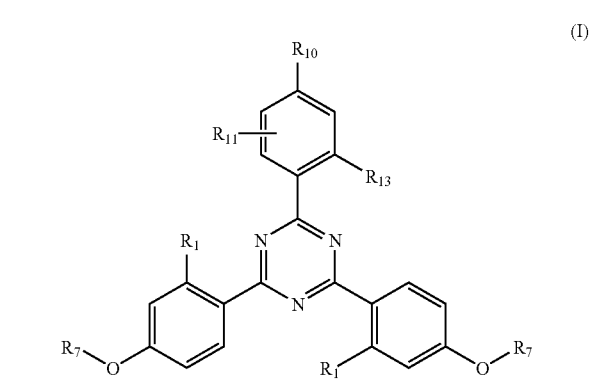

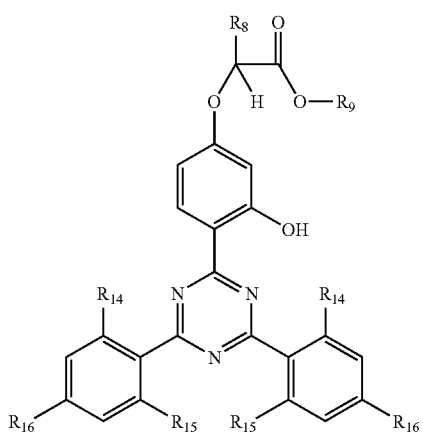

(Ib)

in which
R$_1$ are independently of each other H, OR$_7$ or OH, with the proviso that at least one of R$_1$ or R$_{13}$ is OH;
R$_7$ are independently of each other hydrogen, C$_1$-C$_{12}$alkyl or a radical of formula III,

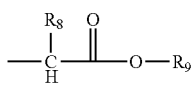

(III)

wherein in formula I at least one R$_7$ is a radical of formula III; R$_8$ is hydrogen,
C$_1$-C$_{18}$alkyl, C$_5$-C$_{12}$cycloalkyl, C$_2$-C$_{18}$alkenyl, phenyl, C$_7$-C$_{11}$phenylalkyl, C$_7$-C$_{11}$alkylphenyl, C$_1$-C$_{18}$alkyl substituted by phenyl, OH or halogen; C$_1$-C$_{18}$alkoxy, C$_5$-C$_{12}$cycloalkoxy, C$_3$-C$_{18}$alkenyloxy or COOH;
R$_9$ is C$_{20}$-C$_{60}$ alkyl, C$_{20}$-C$_{60}$alkyl which is substituted in ω position with a OH group or C$_{20}$-C$_{60}$alkenyl or a group of formula (IV),

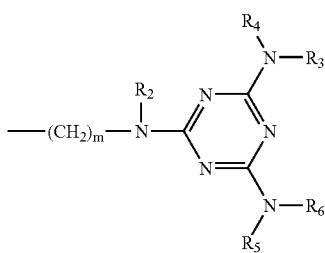

(IV)

wherein m is a number from 1 to 20;
R$_2$, R$_3$, R$_4$, R$_5$ and R$_6$ are independently of each other hydrogen, C$_1$-C$_{38}$alkyl which is unsubstituted or substituted by hydroxy or C$_1$-C$_8$alkoxy; or
C$_1$-C$_{38}$alkyl which is interrupted by an oxygen atom or a N(C$_1$-C$_{18}$)alkyl group; or
phenyl or C$_7$-C$_{12}$phenylalkyl which are unsubstituted or substituted by hydroxy or C$_1$-C$_8$alkyl;
R$_{10}$ is hydrogen, C$_1$-C$_4$alkyl, Cl, phenyl or a group —OR$_7$;
R$_{11}$ is hydrogen or methyl;
R$_{13}$ is hydrogen, methyl, OH or a group OR$_7$;

R$_{14}$ and R$_{15}$ are independently hydrogen, C$_1$-C$_8$alkyl, Cl or a group OR$_7$; and
R$_{16}$ is is hydrogen, C$_1$-C$_8$alkyl, Cl or phenyl.

3. A compound according to claim 1 conforming to formula (I), wherein the R$_7$ are independently of each other hydrogen, C$_1$-C$_{12}$alkyl or a radical of formula (III),

(III)

wherein in formula (I) at least one R$_7$ is a radical of formula (III);
R$_8$ is hydrogen or C$_1$-C$_8$alkyl;
Y is —CO— or C$_1$-C$_2$alkylene;
R$_9$, if Y is —CO—, is C$_{20}$-C$_{60}$ alkyl, C$_{20}$-C$_{60}$alkyl substituted by OH and/or interrupted by O, or is a group of formula (IV),

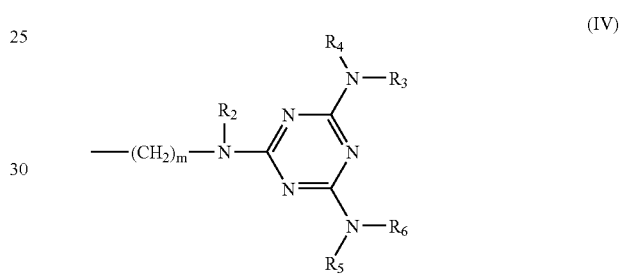

(IV)

wherein m is a number from 2 to 12;
R$_9$, if Y is alkylene, is C$_{20}$-C$_{60}$alkanoyl;
R$_2$, R$_3$, R$_4$, R$_5$ and R$_6$ are independently of each other hydrogen, C$_1$-C$_{18}$alkyl or
C$_4$-C$_{12}$hydroxyalkyl or C$_4$-C$_{12}$alkoxyalkyl;
R$_{10}$ is hydrogen or a group —OR$_7$;
R$_{11}$ and R$_{18}$ independently are hydrogen or methyl; and
R$_{13}$ is hydrogen, OH or methyl.

4. A compound according to claim 3 wherein
R$_1$ is OH;
R$_7$ is hydrogen or methyl or a radical of formula (III),

(III)

R$_8$ is hydrogen or C$_1$-C$_4$alkyl;
R$_{10}$ is hydrogen, methyl or a group —OR$_7$;
R$_{11}$ and R$_{18}$ are hydrogen; and
R$_{13}$ is hydrogen, OH or methyl.

5. A composition protected against the permeation of ultraviolet radiation comprising
 (a) an organic polymer material, and
 (b) at least one compound of formula (I) or (Ib) according to claim 1 or a mixture thereof.

6. A composition according to claim 5 which is a plastic container or film or sheet which protects against the deleterious effects of ultraviolet radiation and wherein component (a) is a clear or lightly colored plastic material.

7. A plastic container or film according to claim 6 which is a food packaging material or a greenhouse film.

8. A composition according to claim 5 wherein the clear or lightly colored plastic is a polyolefin, a polyester, a polyvinylalcohol, a polyvinylacetate, a polycarbonate, a polyamide, an acrylic (co)polymer, an acryl-butadiene-styrene terpolymer or a polyamide.

9. A plastic container or film according to claim 6 wherein the thickness of the film is from 10 μm to 100 μm and the thickness of the plastic container is from 200 μm to 1000 μm.

10. A composition according to claim 5 wherein component (b) is present in an amount of from 0.005% to 10% by weight of component (a).

11. A plastic container or film or sheet according to claim 6 which is a multilayer construction of 2 to 7 polymer layers containing the compound of formula (I) or (Ib) or a mixture thereof in at least 1 layer.

12. A plastic container or film according to claim 6 which contains an additional additive selected from phenolic antioxidants, sterically hindered amines, phosphites, phosphonites, flame retardants and iron based oxygen absorbers.

13. Method of protecting the content of a greenhouse or a package of foodstuffs, beverages, pharmaceuticals, cosmetics, or personal care products from the deleterious effects of ultraviolet radiation, which method comprises shielding said content under a plastic container or film which contains a compound of formula (I) or (Ib) according to claim 1 or a mixture thereof.

14. An hydroxyphenyltriazine compound of formula (I) or (Ib)

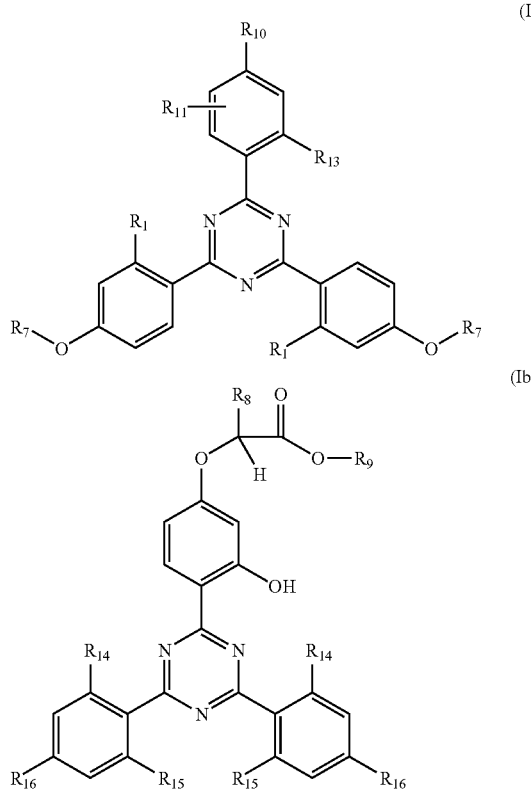

$R_1$ are independently of each other H or $OR_7$, with the proviso that at least one of $R_1$ or $R_{13}$ is OH;

$R_7$ are independently of each other hydrogen, $C_1$-$C_{12}$alkyl or a radical of formula (III),

wherein in formula (I) at least one $R_7$ is a radical of formula (III);

$R_8$ is hydrogen, $C_1$-$C_{18}$alkyl, $C_5$-$C_{12}$cycloalkyl, $C_2$-$C_{18}$alkenyl, phenyl, $C_7$-$C_{11}$phenylalkyl, $C_7$-$C_{11}$alkylphenyl, $C_1$-$C_{18}$alkyl substituted by phenyl, OH or halogen; $C_1$-$C_{18}$alkoxy, $C_5$-$C_{12}$cycloalkoxy, $C_3$-$C_{18}$alkenyloxy or COOH;

Y is —CO—;

$R_9$ is a group of formula (IV),

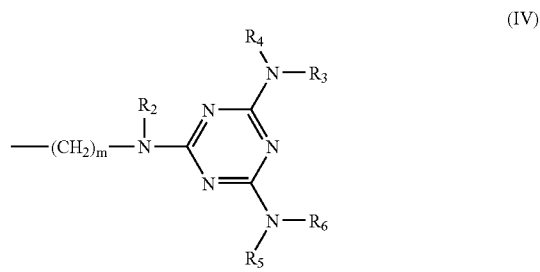

wherein m is a number from 1 to 20;

$R_2$, $R_3$, $R_4$, $R_5$ and $R_6$ are independently of each other hydrogen, $C_1$-$C_{38}$alkyl which is unsubstituted or substituted by hydroxy or $C_1$-$C_8$alkoxy; or $C_1$-$C_{38}$alkyl which is interrupted by an oxygen atom or a $N(C_1$-$C_{18})$alkyl group; or phenyl or $C_7$-$C_{12}$phenylalkyl which are unsubstituted or substituted by hydroxy or $C_1$-$C_8$alkyl;

$R_{10}$ is hydrogen, $C_1$-$C_4$alkyl, Cl, phenyl or a group —$OR_7$;

$R_{11}$ is hydrogen or methyl;

$R_{13}$ is hydrogen, methyl, OH or $OR_7$;

$R_{14}$ and $R_{15}$ are independently hydrogen, $C_1$-$C_8$alkyl, Cl or a group $OR_7$;

$R_{16}$ is is hydrogen, $C_1$-$C_8$alkyl, Cl or phenyl; and $R_{18}$ is hydrogen or $C_1$-$C_8$alkyl.

* * * * *